United States Patent
DeVita et al.

(10) Patent No.: US 7,468,437 B2
(45) Date of Patent: Dec. 23, 2008

(54) PHENYL PYRROLIDINE ETHER TACHYKININ RECEPTOR ANTAGONISTS

(75) Inventors: Robert J. DeVita, Westfield, NJ (US); Peter Lin, Edison, NJ (US); Sander G. Mills, Scotch Plains, NJ (US); Jonathan R. Young, Southborough, MA (US)

(73) Assignee: Merck & Co., Inc., Rahway, NJ (US)

( * ) Notice: Subject to any disclaimer, the term of this patent is extended or adjusted under 35 U.S.C. 154(b) by 301 days.

(21) Appl. No.: 10/572,444

(22) PCT Filed: Sep. 24, 2004

(86) PCT No.: PCT/US2004/031294

§ 371 (c)(1), (2), (4) Date: Mar. 17, 2006

(87) PCT Pub. No.: WO2005/032464

PCT Pub. Date: Apr. 14, 2005

(65) Prior Publication Data

US 2007/0043015 A1 Feb. 22, 2007

Related U.S. Application Data

(60) Provisional application No. 60/507,211, filed on Sep. 30, 2003.

(51) Int. Cl.
| | |
|---|---|
| *C07D 239/00* | (2006.01) |
| *C07D 213/04* | (2006.01) |
| *C07D 207/00* | (2006.01) |
| *C07D 233/00* | (2006.01) |
| *C07D 333/02* | (2006.01) |
| *C07D 321/00* | (2006.01) |
| *C07D 307/00* | (2006.01) |
| *A01N 43/58* | (2006.01) |
| *A01N 43/64* | (2006.01) |
| *A61K 31/41* | (2006.01) |
| *A61K 31/38* | (2006.01) |
| *A61K 31/335* | (2006.01) |

(52) U.S. Cl. .......... 544/358; 544/224; 544/242; 548/300.1; 548/400; 548/215; 548/356.1; 546/249; 546/250; 546/255; 549/29; 549/200; 549/429; 514/247; 514/277; 514/359; 514/430; 514/438; 514/449; 514/235.5; 514/249; 514/254.01; 514/326

(58) Field of Classification Search ............ 514/235.5, 514/247, 249, 254.01, 277, 326, 343, 359, 514/374, 376, 383, 392, 430, 422, 438, 449; 544/141, 224, 236, 242, 372; 546/208, 210, 546/221, 249, 250, 255, 276.4; 548/215, 548/229, 255, 266.2, 300.1, 314.7, 356.1, 548/400, 518; 549/29, 200, 429
See application file for complete search history.

(56) References Cited

U.S. PATENT DOCUMENTS 6,166,037 A * 12/2000 Budhu et al. ............ 514/326
6,458,787 B1 10/2002 Martins et al.

FOREIGN PATENT DOCUMENTS

EP 1 386 912 A1 4/2004

OTHER PUBLICATIONS

Hale, et al. "1,3,4-Trisubstituted pyrrolidine CCR5 Receptor Antagonists. Part 1: Discovery of the Pyrrolidine Scaffold and Determination of Its Stereochemical Requirements", Bioorganic & Medicinal Chemistry Letters, vol. 11, pp. 1437-1440 (2001).*
DeVane, "Substance P: A New Era, a New Role", Pharmacotherapy, vol. 21(9), pp. 1061-1069 (2001).*
Lowe, "The Painful History of Substance P", Corante, Aug. 25, 2005.*
Ebner, et al. "The role of substance P in stress and anxiety responses", Amino Acids, vol. 31, pp. 251-272 (2006).*

* cited by examiner

*Primary Examiner*—Kamal A Saeed
*Assistant Examiner*—Samantha L Shterengarts
(74) *Attorney, Agent, or Firm*—Yong Zhao; Valerie J. Camara

(57) ABSTRACT

The present invention is directed to certain phenyl pyrrolidine ether compounds which are useful as neurokinin-1 (NK-1) receptor antagonists, and inhibitors of tachykinin and in particular substance P. The invention is also concerned with pharmaceutical formulations comprising these compounds as active ingredients and the use of the compounds and their formulations in the treatment of certain disorders, including emesis, depression, and anxiety.

13 Claims, No Drawings

PHENYL PYRROLIDINE ETHER TACHYKININ RECEPTOR ANTAGONISTS

CROSS REFERENCE TO RELATED APPLICATIONS

This application is a U.S. national Phase application under 35.U.S.C. § 371 of PCT Application No. PCT/US2004/031294, filed Sep. 24, 2004, which claims priority under 35 U.S.C. 119 to U.S. No. 60/507,211, filed Sep. 30, 2003.

BACKGROUND OF THE INVENTION

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence. In addition to substance P, the known mammalian tachykinins include neurokinin A and neurokinin B. The current nomenclature designates the receptors for substance P, neurokinin A, and neurokinin B as neurokinin-1 (NK-1), neurokinin-2 (NK-2), and neurokinin-3 (NK-3), respectively.

Evidence has been reviewed for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyperreflexia.

It has furthermore been suggested that tachykinin receptor antagonists have utility in the following disorders: anxiety, depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosus, ophthalmic diseases such as conjunctivitis, vernal conjunctivitis, and the like, and cutaneous diseases such as contact dermatitis, atopic dermatitis, urticaria, and other eczematoid dermatitis.

SUMMARY OF THE INVENTION

The present invention is directed to compounds of the structural formula I:

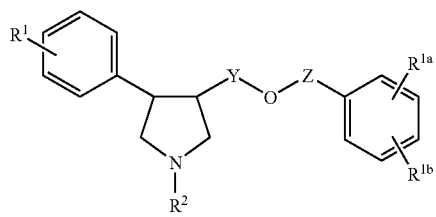

or a pharmaceutically acceptable salt thereof, wherein $R^1$, $R^{1a}$, $R^{1b}$, $R^2$, Y, and Z are hereinafter defined. The compounds of structure I are useful as neurokinin-1 (NK-1) receptor antagonists, and inhibitors of tachykinin and in particular substance P. The invention is also concerned with pharmaceutical formulations comprising these novel compounds as active ingredients and the use of the novel compounds and their formulations in the treatment of certain disorders, such as emesis, depression (mood disorders), and anxiety.

DETAILED DESCRIPTION OF THE INVENTION

The instant invention is directed to compounds of the structural formula I:

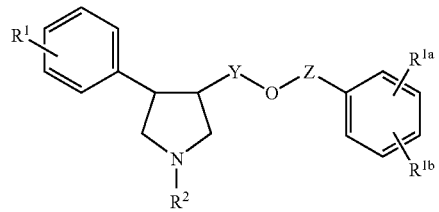

wherein:

$R^1$, $R^{1a}$ and $R^{1b}$ are independently selected from the group consisting of H, F, Cl, Br, I, $CH_3$, $CF_3$, OH, $OCH_3$, $NH_2$, $NHCH_3$, SH, and $SCH_3$;

$R^2$ is selected from the group consisting of H, $R^4$, $COR^4$, and $SO_2R^4$;

Y is a bond, $CHCH_3$, or $CH_2$;

Z is selected from the group consisting of $CH_2$, $CHCH_3$, CO, $COCH_2$, $SO_2$, and $SO_2CH_2$;

$R^4$ is independently selected from the group consisting of H, $C_{1-6}$alkyl, phenyl optionally substituted by $R^6$, benzyl, O—$C_{1-6}$alkyl, O-benzyl, N($R^5$)—$C_{1-6}$alkyl, N($R^5$)-benzyl,

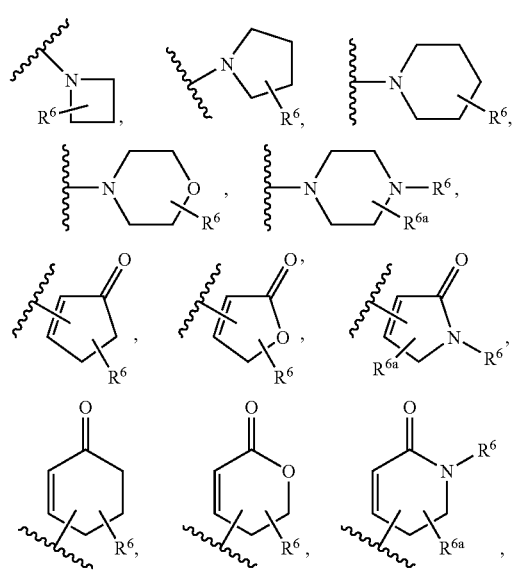

-continued

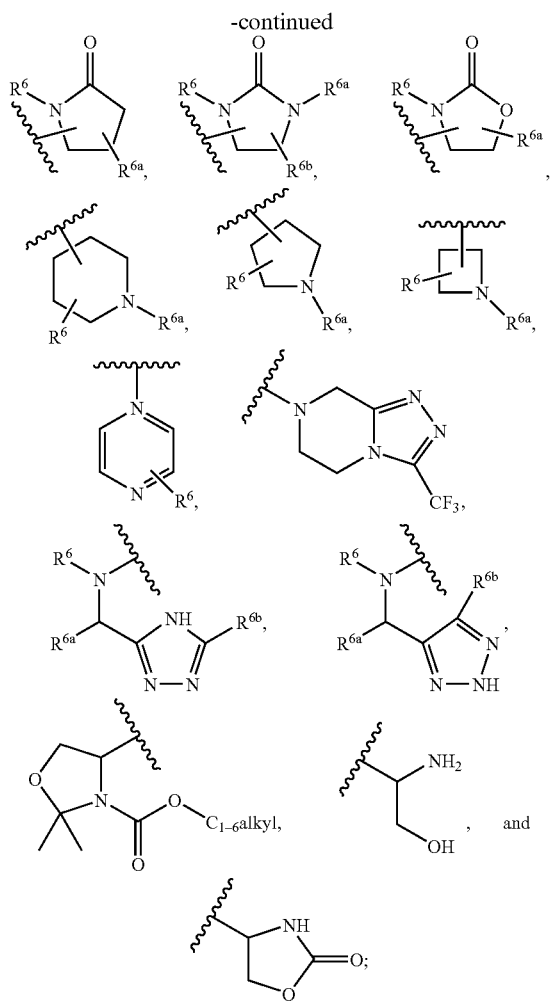

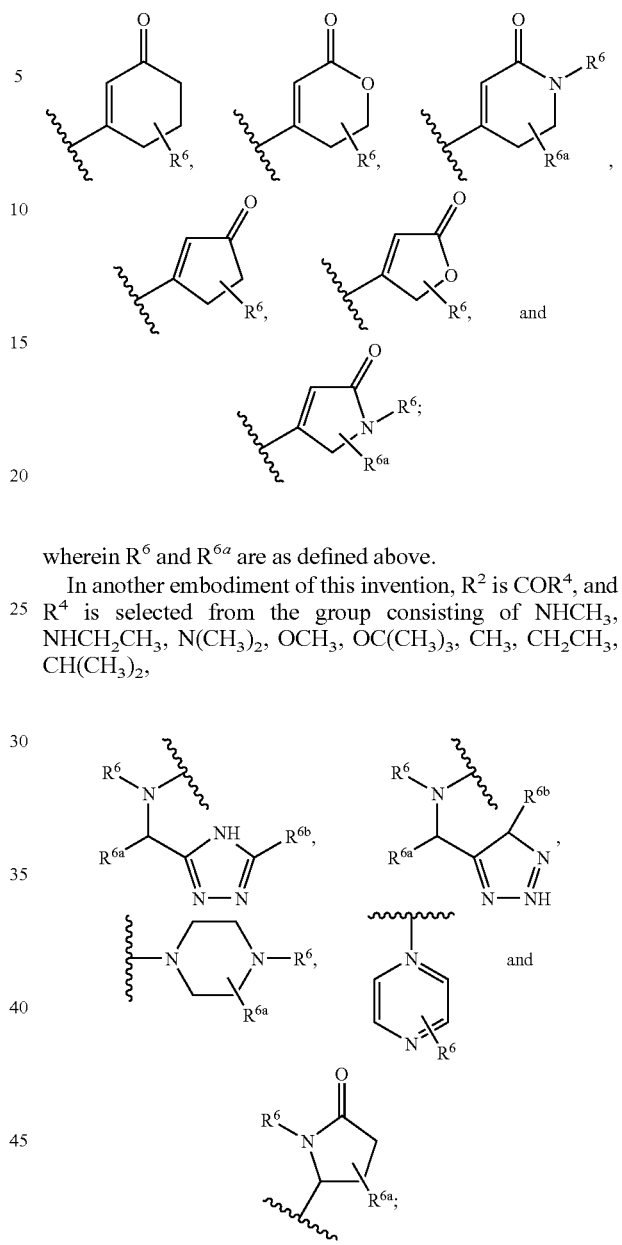

wherein $R^6$ and $R^{6a}$ are as defined above.

In another embodiment of this invention, $R^2$ is $COR^4$, and $R^4$ is selected from the group consisting of $NHCH_3$, $NHCH_2CH_3$, $N(CH_3)_2$, $OCH_3$, $OC(CH_3)_3$, $CH_3$, $CH_2CH_3$, $CH(CH_3)_2$, $R^5$ is H or $C_{1-6}$alkyl;

$R^6$, $R^{6a}$, and $R^{6b}$ are independently selected from the group consisting of H, F, Cl, $CF_3$, $OCH_3$, $CH_3$, $COCH_3$, $CO_2CH_3$, $CH_2CONH_2$, $CONH_2$, $CONHCH_3$, and $SO_2CH_3$;

and pharmaceutically acceptable salts thereof.

An embodiment of this invention is directed to compounds of the formula Ia:

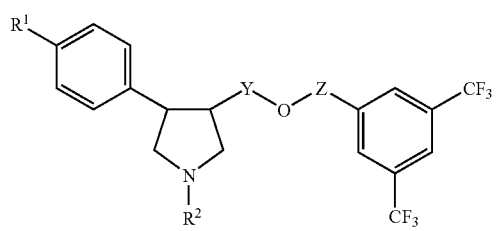

Ia wherein Y, Z, $R^1$, $R^2$, and $R^3$ are as defined herein.

In another embodiment of the instant invention, Y is a bond, and $R^1$ is H or F.

In another embodiment of this invention, $R^2$ is $R^4$, and $R^4$ is selected from the group consisting of:

wherein $R^6$, $R^{6a}$, and $R^{6b}$ are as defined above.

A further embodiment of this invention is directed to a compound which is selected from the group consisting of:

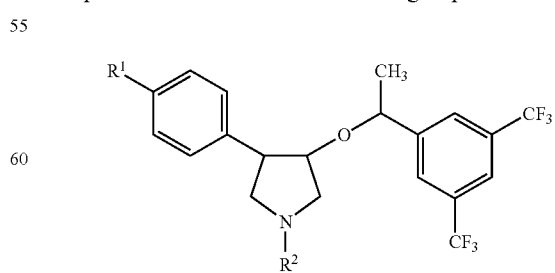

wherein $R^2$ and $R^1$ are selected from the table below:

| R² | R¹ |
|---|---|
| acetyl (CH₃C(O)-) | F |
| acetyl (CH₃C(O)-) | H |
| 3-methyl-cyclopent-2-enone | F |
| 2,3-dimethyl-cyclopent-2-enone | F |
| 3-methyl-cyclopent-2-enone | H |
| 3-methyl-5-methyl-cyclopent-2-enone | F |
| 3-methyl-5-hydroxy-cyclopent-2-enone | F |
| 3-methyl-4-methyl-cyclopent-2-enone | F |
| 3-methyl-4-hydroxy-cyclopent-2-enone | F |
| 4-methyl-2-oxo-cyclopent-3-enyl acetamide | F |
| methyl 4-methyl-2-oxo-cyclopent-3-ene-1-carboxylate | F |

-continued

| R² | R¹ |
|---|---|
| N-methyl 4-methyl-2-oxo-cyclopent-3-ene-1-carboxamide | F |
| 2-hydroxy-2,4-dimethyl-cyclopent-3-enone | F |
| H | F |
| N-methylacetamide | F |
| N-ethylacetamide | F |
| N-ethylacetamide | H |
| N-isopropylacetamide | F |
| N-isopropylacetamide | H |
| 4-methyl-2(5H)-furanone | F |
| 4-methyl-3-phenyl-2(5H)-furanone | F |
| 1,4-dimethyl-3-pyrrolin-2-one | F |
| 1,5-dimethyl-pyrrolidin-2-one | F |

-continued
| R² | R¹ |
|---|---|
| 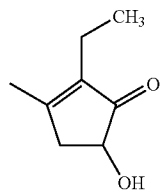 | F |
| 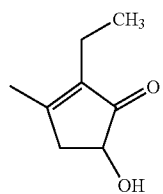 | F |
| 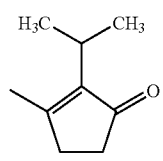 | F |
| 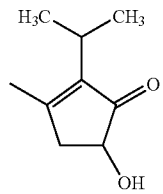 | F |
| 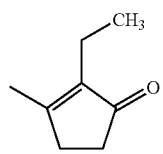 | F |
| 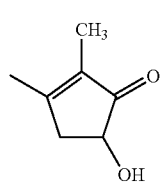 | F |
| 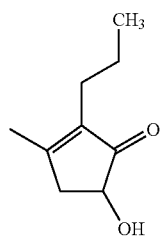 | F |
| 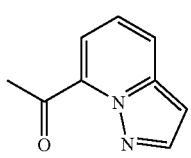 | F |
-continued
| R² | R¹ |
|---|---|
| 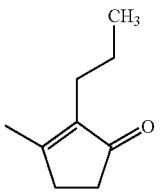 | F |
| 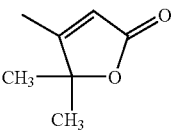 | F |
| 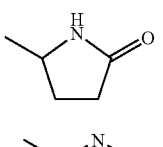 | F |
| 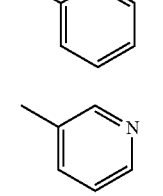 | F |
| 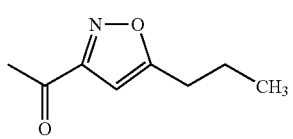 | F |
| 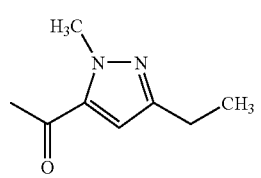 | F |
| 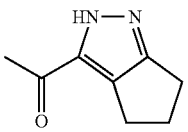 | F |
| 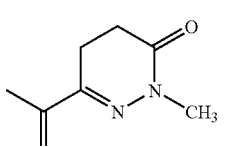 | F |
| 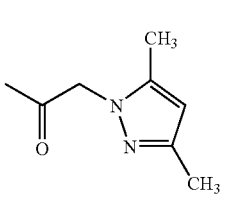 | F |

| R² | R¹ |
|---|---|
| (1-methyl-1H-pyrazol-4-yl) acetyl | F |
| (pyrazolo[1,5-a]pyrimidin-3-yl) acetyl | F |
| (1-methyl-1H-pyrazol-5-yl) acetyl | F |
| (1H-benzimidazol-2-yl) acetyl | F |
| 1-(3-methyl-1H-pyrazol-1-yl)butan-3-one | F |
| (pyrimidin-4-yl) acetyl | F |
| (pyrazolo[1,5-a]pyridin-7-yl) acetyl | F |
| (pyrimidin-5-yl) acetyl | F |
| 1-(1H-1,2,4-triazol-1-yl)propan-2-one (methyl) | F |
| (thiophen-2-yl) acetyl | F |

| R² | R¹ |
|---|---|
| 3-acetyl-cyclobutanone | F |
| (furan-2-yl) acetyl | F |
| 1-(3-methyl-1H-pyrazol-1-yl)propan-2-one | F |
| (pyrazin-2-yl) acetyl | F |
| 1-acetyl-1,3-dimethyl-1H-pyrazole | F |
| 1-(3-methyl-1H-1,2,4-triazol-5-yl)propan-2-one | F |
| tert-butyl 4-acetyl-2,2-dimethyloxazolidine-3-carboxylate | H |
| 3-amino-4-hydroxy-butan-2-one | H |
| 3-amino-4-hydroxy-butan-2-one | F |
| 4-acetyl-oxazolidin-2-one | H |

| R² | R¹ |
|---|---|
| ![oxazolidinone-acetyl] | F |
| ![methylpyrazole-propanone] | F | and pharmaceutically acceptable salts thereof.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Preparation

The preparation of compounds of Formula I of the present invention may be carried out in sequential or convergent synthetic routes. Syntheses detailing the preparation of the compounds of Formula I in a sequential manner are presented in the following reaction schemes. The skills required in carrying out the reaction and purification of the resulting reaction products are known to those skilled in the art. Purification procedures includes crystallization, normal phase or reverse phase chromatography.

Methods for preparing the compounds of this invention are illustrated in the following Schemes and Examples wherein the variables in the schemes are as defined with reference to the variables at the corresponding positions of the general structural formula I and Ia herein.

A general approach to the synthesis of substituted 3-hydroxypyrrolidines is outlined in Scheme I. Nitrogen protected 2,5-dihydropyrroles II, utilizing protecting groups such as the t-butoxycarbonyl (BOC) or benzyloxycarbonyl (CBZ), may be epoxidized by methods known to those skilled in the art to compounds of general structure III by a variety of oxidizing reagents such as organic peroxides in the presence of a catalyst or organic peracids. This epoxide intermediate may be opened by a variety of organometallic species such as a Grignard, organolithium and others with or without the presence of a catalyst such as CuI. The products of the reactions are presumably the result of a trans diaxial opening to provide racemic products with a trans relative stereochemistry at the 3,4-positions of the resulting substituted pyrrolidine IV.

SCHEME I

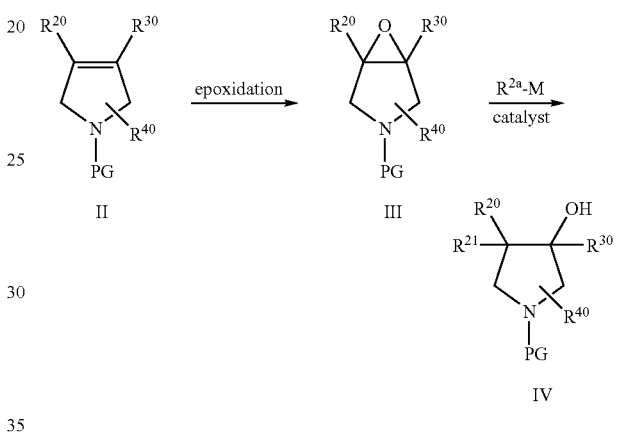

This racemic mixture may be separated by a variety or combination of methods known to those skilled in the art to provide single enantiomers of the 3,4-substituted pyrrolidines IV (Scheme II). Presumably, chiral catalyst systems may be developed which would provide single enantiomers IVa or IVb of the desired stereochemistry as intermediates for NK-1 antagonists from the meso epoxide intermediates III (eq. 1). Similarly, stoichiometric chiral additives such as sparteine or other additives may provide enantiomerically enriched mixtures of the intermediates IVa or IVb. Alternatively, one can resort to preparative chiral HPLC methods for the isolation of both enantiomers IVa and IVb (eq.2). Another method may entail esterification with a chiral acid to form a mixture or diastereomers which may be separated by crystallization or chromatography, for example. Separate hydrolysis of these diastereomeric esters would provide enantiomeric trans pyrrolidine alcohols IVa and IVb, respectively. Another method for separation of enantiomers known to those skilled in the art is the enzymatic acylation of alcohols (eq. 3). Treatment of the racemic mixture IV with a lipase enzyme in an organic solvent with an acylation precursor such as vinyl acetate may lead to the enantiospecific acylation of one enantiomer with the opposite enantiomer remaining unchanged. Simple chromatographic separation of alcohol from acetate and hydrolysis of the acetate may provide the enantiomers IVa and IVb, respectively. (The converse enzymatic hydrolysis is also applicable by conversion of the mixture of alcohols IV to the acetate esters then enzymatic hydrolysis to the alcohol IVb, for example, while the enantiomeric acetate remains unchanged). These are but a few of the possible methods by which racemic mixtures of alcohols of general structure IV may be separated to enantiomerically enriched or pure form.

SCHEME II

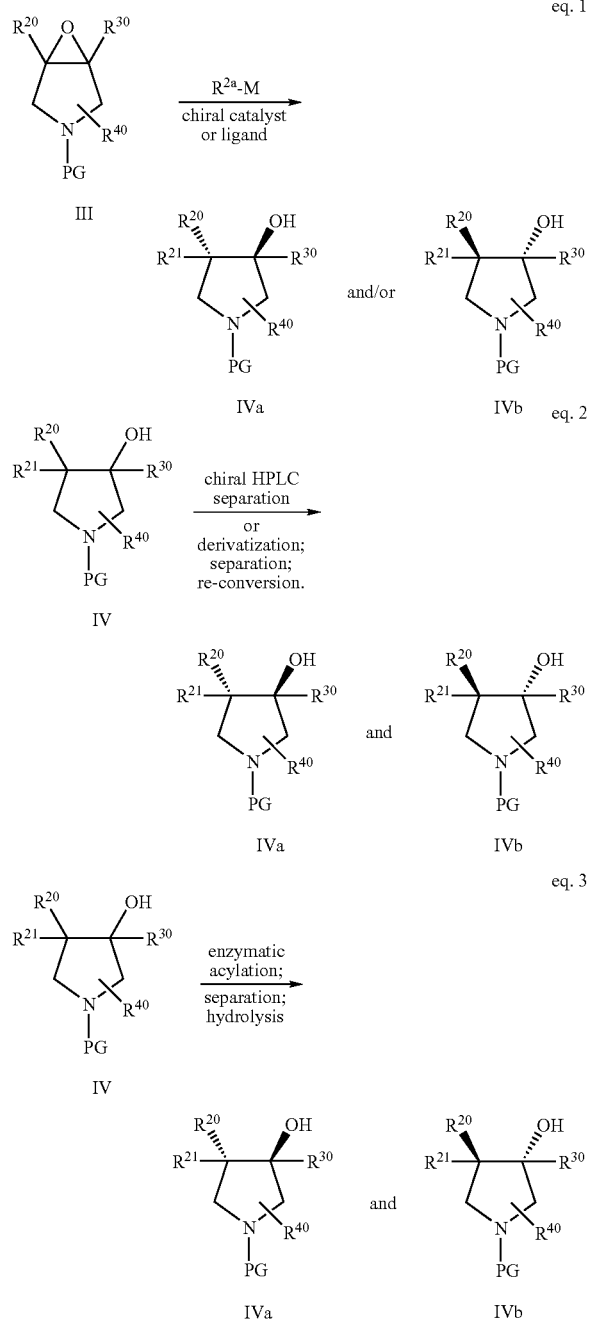

Pyrrolidine alcohols of general structure IV may be converted to ether intermediates V by a variety of methods known to those skilled in the art (Scheme III). For example, reaction of intermediates IV and an alcohol derivative VI with a leaving group X such as the trichloroacetimidate group (or others known to those skilled in the art) with an acid catalyst such as triflic (trifluoromethanesulfonic) acid or $HBF_4$ may result in conversion to the corresponding pyrrolidine ethers V. Removal of the nitrogen protecting group by methods known to those skilled in the art provides pyrrolidine intermediates of general structure VII ready for derivatization on the pyrrolidine nitrogen.

SCHEME III

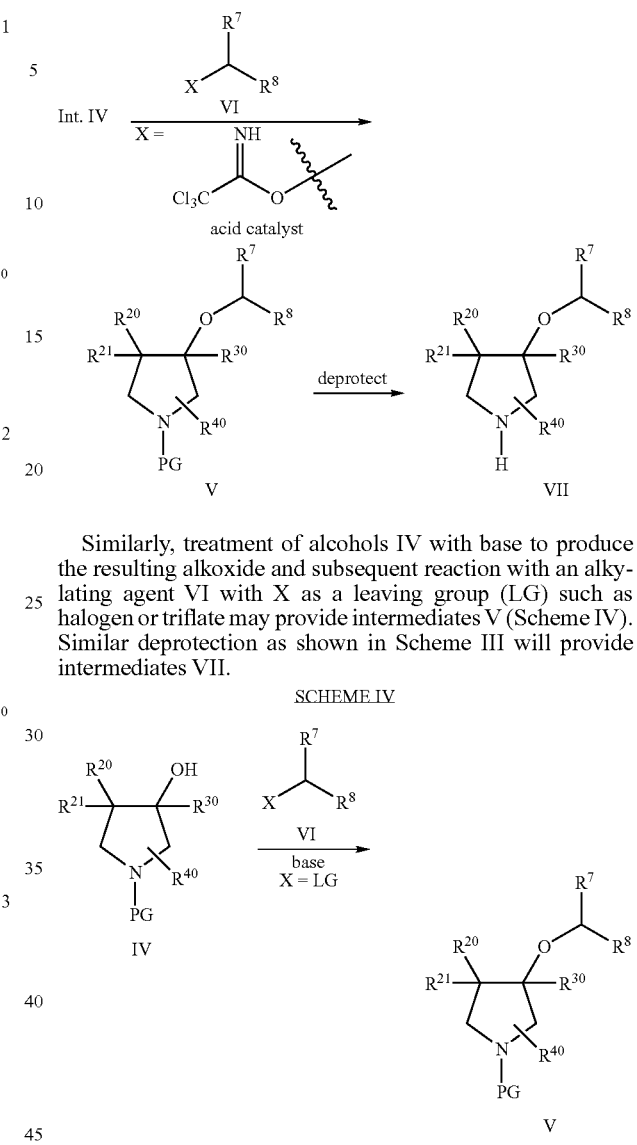

Similarly, treatment of alcohols IV with base to produce the resulting alkoxide and subsequent reaction with an alkylating agent VI with X as a leaving group (LG) such as halogen or triflate may provide intermediates V (Scheme IV). Similar deprotection as shown in Scheme III will provide intermediates VII.

SCHEME IV

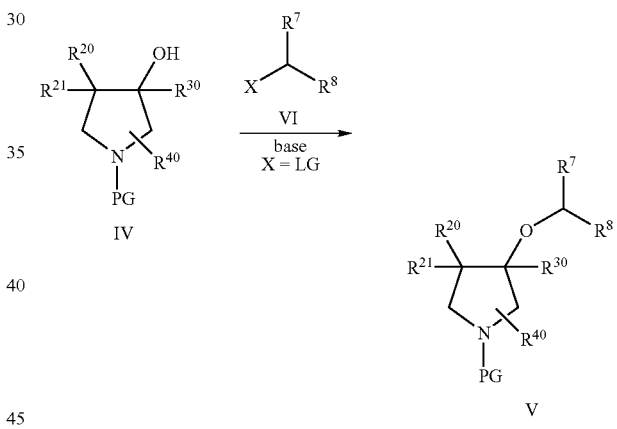

An alternative multi-step method to produce ether intermediates V is outlined in Scheme V. Esterification of the alcohol intermediate IV with a carboxylic acid or acid chloride VIII (X=OH, Cl, etc.), by a variety of methods known to those skilled in the art, may provide ester intermediates IX. Olefination of such esters by a variety of reagents such as "dimethyltitanocene" (Petasis reagent) or "Tebbe Reagent," known to those skilled in the art, may produce enol ether intermediates X. Alternatively, enol ethers X may be prepared directly from alcohol intermediates IV by condensation of aldehydes, ketones or related intermediates in the presence of a catalyst with subsequent loss of water. The resulting enol ethers X may be converted to ethers V by a variety of methods known to those skilled in the art such as hydrogenation in the presence of metal catalyst, hydroboration or other similar hydration reactions or reduction via a silicon hydride or other hydride donor in the presence of a catalyst such as an acid. In this way, intermediates of general structure V may be prepared from the enol ether intermediates X by a multistep sequence. As discussed earlier, use of chiral reagent systems for the reduction of enol ether intermediates X may provide improved enantio- or diastereoselectivity in the production of intermediates pyrrolidine ethers V.

SCHEME V

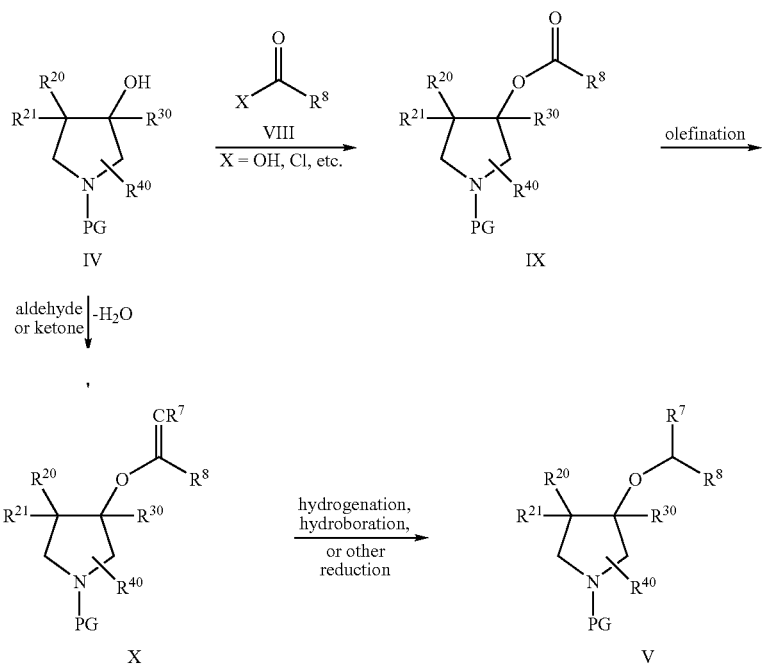

Intermediates V, having trans relative stereochemistry at the 3,4-positions of the pyrrolidine ring, may be produced from alcohol intermediates IV having the corresponding 3,4-trans pyrrolidine stereochemistry. Compounds with cis relative pyrrolidine stereochemistry at the 3,4-positions may be prepared as outlined in Scheme VI. Reaction of the trans alcohols IV, in racemic or chiral form, with an appropriate carboxylic acid VIII in the presence an azodicarboxylate reagent such as diisopropylazodicarboxylate and a phosphine such as triphenyl phosphine in an appropriate solvent may allow conversion to the ester intermediates IX by inversion of stereochemistry at the 3-hydroxyl group of the pyrrolidine ring. This will result in cis relative stereochemistry of resulting intermediates cis IX. Enantiomerically pure alcohols such as intermediates IVa, for example, will result in enantiomerically pure 3,4-cis pyrrolidine intermediates IXa. Similarly the antipode of intermediate IXb can be prepared from alcohol intermediate IVb. Conversion to the enol ether intermediates X and ether intermediates V as shown in Scheme V will result in those amine intermediates VII of cis relative stereochemistry at the 3,4-positions of the pyrrolidine ring.

SCHEME VI

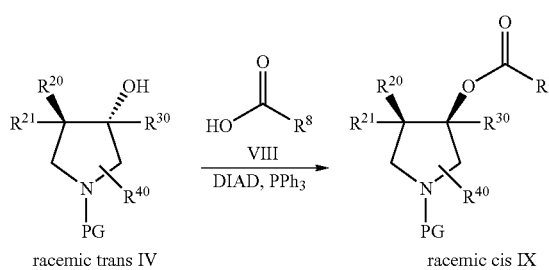

-continued

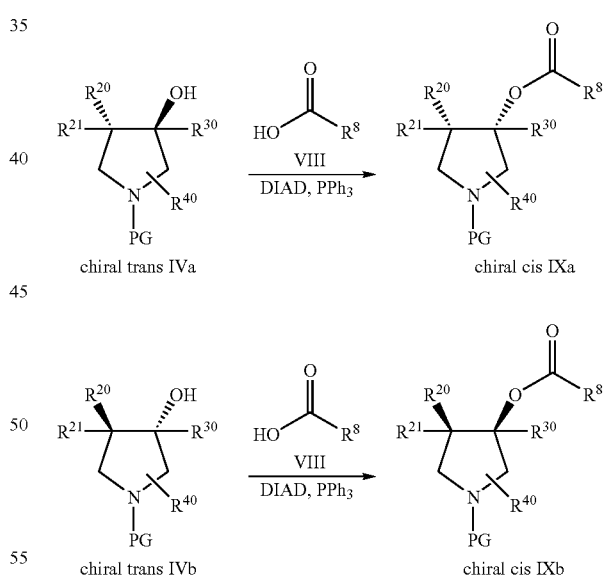

Intermediates of general structure VII, prepared in 3,4-cis or trans relative stereochemistry may be derivatized on the nitrogen atom at position-1 with a variety of groups $R^1$ as indicated in Scheme VII. Amine derivatives are useful in a variety of reactions to prepare other functional groups including carboxamides, sulfonamides, ureas, amidines, guanidines, vinylogous amides, vinylogous urethanes and vinylogous ureas by a variety of methods known to those skilled in the art.

SCHEME VII

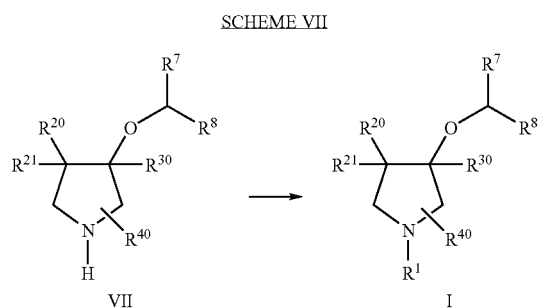

More specifically, intermediates of general structure VII may be reacted with carboxylic acids or derivatives such as acid chlorides in the presence of base or a coupling reagent to form carboxamide derivatives of structure I, shown as structure XI. Similarly, reaction of intermediates VII with sulfonyl chlorides may provide sulfonamide derivatives XII (Scheme VIII).

SCHEME VIII

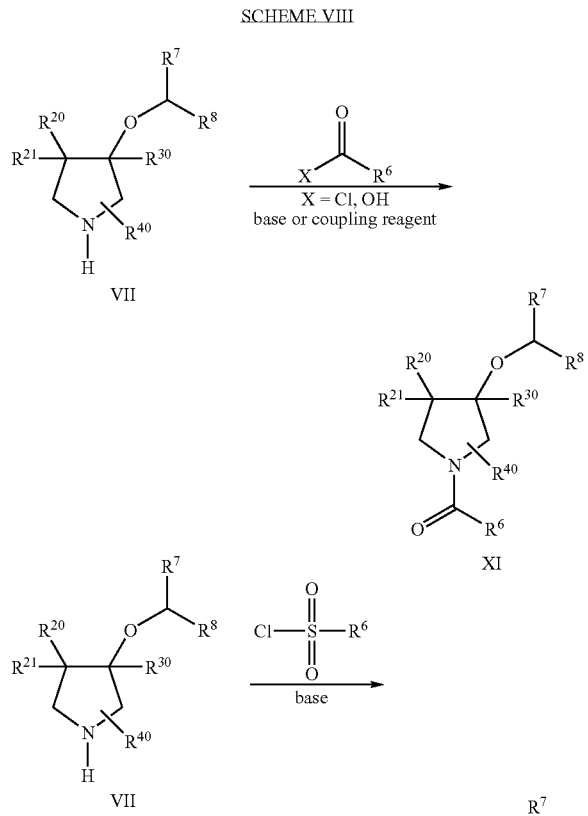

Reaction of amines VII with carbamoyl chlorides or isocyanates with or without base will provide urea derivatives XIII as shown in Scheme IX. Alternatively, amine intermediates VII may react with phosgene or equivalent reagents such as CDI or triphosgene to provide intermediate carbamoyl chlorides XIV. These intermediates XIV may subsequently react with amines to provide ureas of general structure XIII. Similarly, carbamates (urethanes) may be prepared analogously from the above intermediates by choosing appropriate chloroformates for reactions with VII or alcohol for reaction with intermediates XIV known to those skilled in the art (products not shown).

SCHEME IX

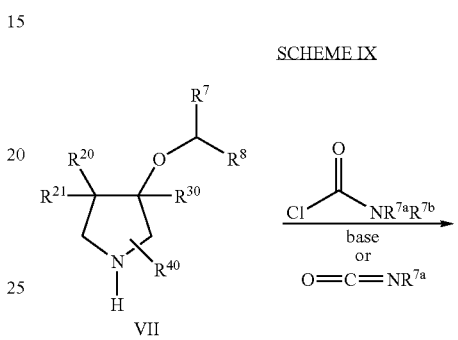

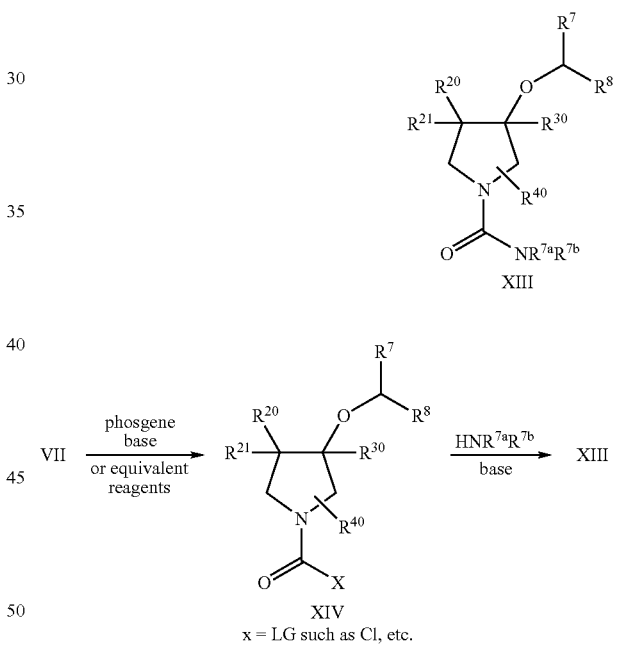

Vinylogous amide derivatives of general structure XV may be prepared from intermediates amines VII by condensation with cyclic or acyclic 1,3-diketone derivatives XVI (1,3-cyclopentanedione derivatives shown) in the presence of an acid catalyst with subsequent loss of water. Similarly, condensation of intermediates VII with derivatives XVII containing a leaving group (X=Cl, etc.) by treatment in the presence of a base in an appropriate solvent may provide derivatives XV. Again, these examples may be extended to related intermediates XVI and XVII of smaller or larger rings sizes from appropriate starting materials known to those skilled in the art.

SCHEME X

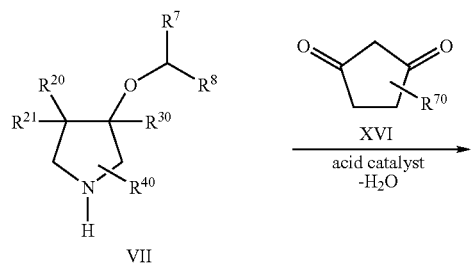

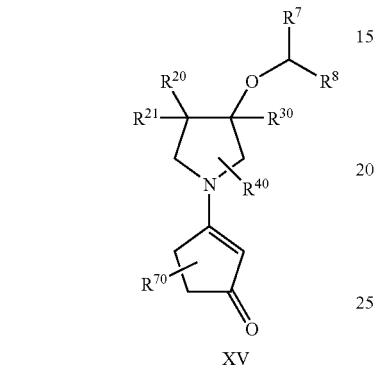

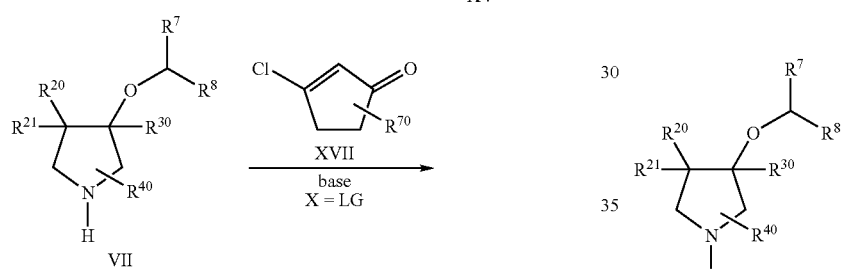

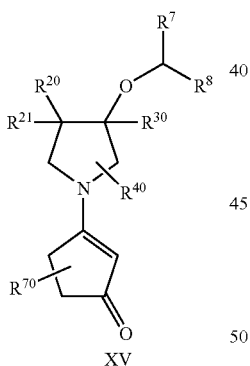

SCHEME XI

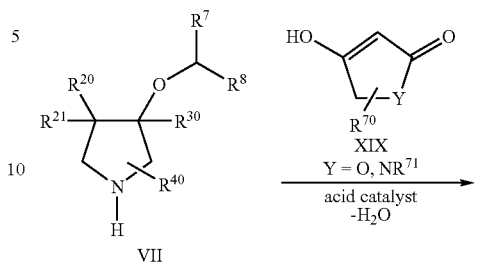

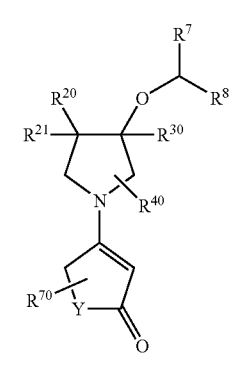

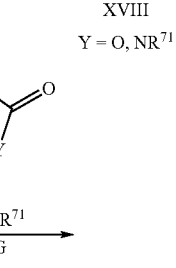

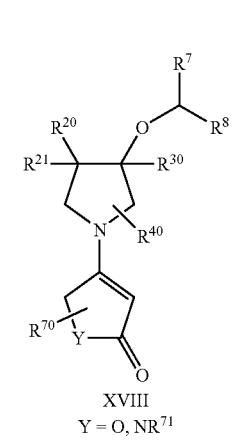

Vinylogous urethane and vinylogous urea derivatives of general structure XVIII may be prepared from intermediates amines VII by condensation with 1,3-ketoester or ketoamide derivatives (tetronic or tetramic acid derivatives XIX; Y=O, or $NR^{7a}$ shown, respectively) in the presence of an acid catalyst with subsequent loss of water. Similarly, condensation of amine intermediates VII with lactone or lactam derivatives XX containing a leaving group (X=Cl, etc.) by treatment in the presence of a base in an appropriate solvent may provide derivatives XVIII. Again, these examples may be extended to similar intermediates XIX and XX of smaller or larger rings sizes from appropriate starting materials known to those skilled in the art.

Amine intermediates VII may react with aryl or heteroaryl halides in the presence of a base with or without metal catalysts such as Pd-catalysts or Cu-catalysts to provide amine derivatives of the present invention I ($R^1$=Aryl or heteroaryl, Scheme XII. In addition, amine intermediates VII may be condensed with aldehydes and ketones to form imines upon loss of water, which upon subsequent hydrogenation in the presence of a metal catalyst or reduction with a hydride reagent, such as sodium borohydride, may produce alkylated amine derivatives I (R=alkyl groups). Alternatively, N-carboxamides (XI) may be reduced under a variety of conditions to alkylated amines I of the present invention.

SCHEME XII

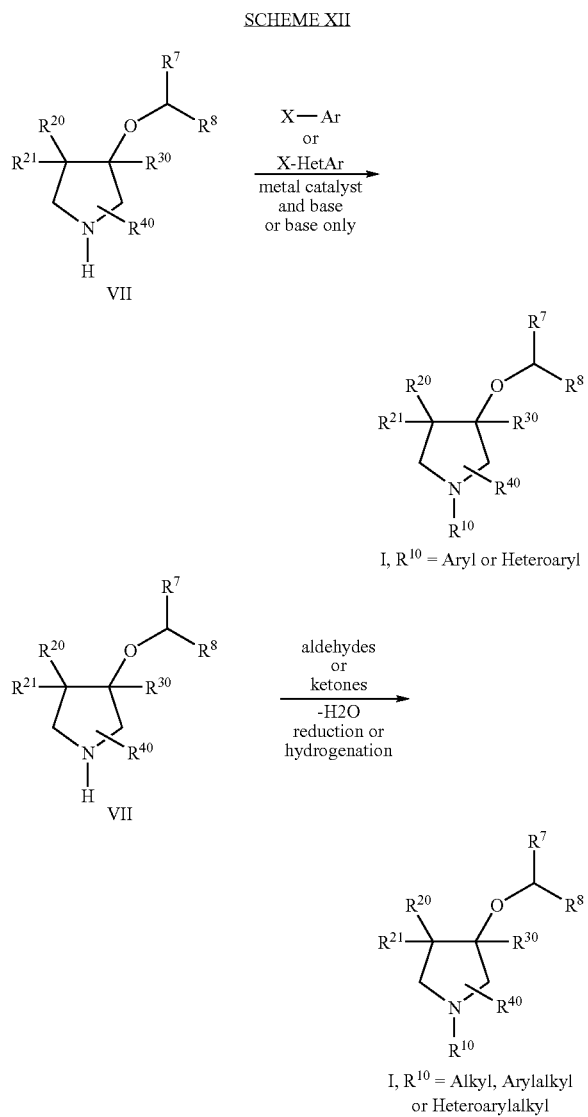

It is noted that in some cases the order of carrying out the foregoing reaction schemes may be varied to facilitate the reaction or to avoid unwanted reaction products. Protecting groups may also be changed to provide intermediates which may facilitate the reaction sequence or avoid unwanted side reactions or by-products. In addition, certain functional group manipulations such as hydrolysis, reduction, oxidation and conversion to other functional groups such as alcohols, carboxamides, carboxylic acids, etc. may be performed on the substituents of intermediates to make new derivatives of the examples described above.

Polymer-bound reagents known to those skilled in the art may be utilized in the above mentioned schemes in place of the solution phase reagents described. Alternatively, substrates may be appended to polymers (for example, in place of a protecting group), carried through several reaction steps and then cleaved from the polymer to afford the desired products.

Pharmacological Activity

The compounds of the present invention are useful in the prevention and treatment of a wide variety of clinical conditions which are characterized by the presence of an excess of tachykinin, in particular substance P, activity. Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculoskeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of the present invention are also of value in the treatment of a combination of the above conditions, in particular in the treatment of combined post-operative pain and post-operative nausea and vomiting.

The compounds of the present invention are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of the present invention are of use in the treatment of emesis induced by antineoplastic (cytotoxic) agents, including those routinely used in cancer chemotherapy, and emesis induced by other pharmacological agents, for example, rolipram. Examples of such chemotherapeutic agents include alkylating agents, for example, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics. Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177-203, especially page 188. Commonly used chemotherapeutic agents include cisplatin, dacarbazine (DTIC), dactinomycin, mechlorethamine, streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163-172].

A further aspect of the present invention comprises the use of a compound of the present invention for achieving a chronobiologic (circadian rhythm phase-shifting) effect and alleviating circadian rhythm disorders in a mammal. The present invention is further directed to the use of a compound of the present invention for blocking the phase-shifting effects of light in a mammal.

The present invention is further directed to the use of a compound of the present invention or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of the present invention or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

The particularly preferred embodiments of the instant invention are the treatment of emesis, depression (mood disorders), and anxiety by administration of the compounds of the present invention to a subject (human or animal) in need of such treatment.

According to a further or alternative aspect, the present invention provides a compound of the present invention for use in the manufacture of a medicament for the treatment of physiological disorders associated with an excess of tachykinins, especially substance P. The present invention further provides a compound of the present invention for use in therapy.

The present invention also provides a method for the treatment or prevention of physiological disorders associated with an excess of tachykinins, especially substance P, which method comprises administration to a patient in need thereof of a tachykinin reducing amount of a compound of the present invention or a composition comprising a compound of the present invention.

As used herein, the term "treatment" or "to treat" refers to the administration of the compounds of the present invention to reduce, ameliorate, or eliminate either the symptoms or underlying cause of the noted disease conditions, in a subject (human or animal) that suffers from that condition or displays clinical indicators thereof.

The term "prevention" or "to prevent" refers to the administration of the compounds of the present invention to reduce, ameliorate, or eliminate the risk or likelihood of occurrence of the noted disease conditions, in a subject (human or animal) susceptible or predisposed to that condition.

Tachykinin Antagonism Assay

The compounds of this invention are useful for antagonizing tachykinins, in particular substance P in the treatment of gastrointestinal disorders, central nervous system disorders, inflammatory diseases, pain or migraine and asthma in a mammal in need of such treatment. This activity can be demonstrated by the following assays.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/ml Herring sperm DNA at 300 V and 950 uF using the IBI GENEZAPPER (IBI). The transfected cells were incubated in CHO media [10% fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol Using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1 N HCl is added. Each well is sonicated at 4° C. and extracted with $CHCl_3$/methanol (1:1). The aqueous phase is applied to a 1 ml Dowex AG 1X8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter.

In particular, the intrinsic tachykinin receptor antagonist activities of the compounds of the present invention may be demonstrated by this assay. The compounds of the following examples have activity in the aforementioned assay in the range of 0.05 nM to 10 μM. The activity of the present compounds may also be demonstrated by the assay disclosed by Lei, et al., *British J. Pharmacol.*, 105, 261-262 (1992).

Compositions

According to a further or alternative aspect, the present invention provides a compound of the present invention for use as a composition that may be administered to a subject in need of a reduction of the amount of tachykinin or substance P in their body.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxy-cetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouth washes and gargles.)

The compounds of the present invention may also be administered by a transdermal patch. Such patches are typically a layered construct employing a drug reservoir layer, a backing layer, optional membrane layers, and an adhesive layer. The backing layer is the outermost layer, and protects the underlying layers from physical damage and air. The drug reservoir layer contains the active and inactive ingredients prior to delivery to the skin of the patient. Inactive ingredients in transdermal patches are commonly oils, glycols, or alcohols, that dissolve or suspend the active ingredients and assist the egress of active ingredients through other layers in the patch system and the skin. The adhesive layer provides an adhesive that keeps the patch affixed to the skin for the desired duration. Transdermal patches commonly are used for extended delivery of active ingredients, often during a period of several days to several weeks.

The compounds of the present invention may also be administered by inhalation. Inhalation devices may used orally wherein the active ingredients are absorbed into the lungs, or they may be used nasally wherein the active ingredients are absorbed into the nasal passages or sinuses. Inhalation devices typically involve the use of powders or sprays, and may contain a propellant, a pump, or other system for inhalation of active ingredients. In the case of powders, the active ingredient can be milled to a fine powder, and typically mixed with lactose. In the case of sprays, the sprayed product is usually a solution or suspension. Spray solutions are typically water soluble products, but may contain other inert ingredients such as propylene glycol or an alcohol. Spray suspensions use a finely milled solid product suspended in an aqueous solution, or a suitably dissolved non-solid product, that may contain other inert ingredients, such as microcrystalline cellulose and an alcohol. Both spray solutions and suspensions typically also contain a preservative, such as benzalkonium chloride or chlorine dioxide. The inhalation products also include a proprietary inhalation device, usually capable of delivering a metered dose of a therapeutically effective amount of active ingredients.

The compositions containing compounds of the present invention may be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms.

The compositions containing compounds of the present invention may also be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individuals body in a therapeutically useful form and therapeutically effective amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The term "therapeutically effective amount" refers to a sufficient quantity of the compounds of the present invention, in a suitable composition, and in a suitable dosage form to treat or prevent the noted disease conditions.

Combinations

The compounds of the present invention may be administered in combination with another substance that has a complimentary effect to the tachykinin and substance P inhibitors of the present invention.

Accordingly, in the prevention or treatment of emesis, a compound of the present invention may be used in conjunction with other anti-emetic agents, especially 5HT$_3$ receptor antagonists, such as ondansetron, granisetron, tropisetron, decadron, and zatisetron, or GABA$_B$ receptor agonists, such as baclofen. Likewise, for the prevention or treatment of migraine a compound of the present invention may be used in conjunction with other anti-migraine agents, such as ergotamines or 5HT$_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents. Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof. Suitable selective serotonin reuptake inhibitors include: fluoxetine, fluvoxamine, paroxetine and sertraline, and pharmaceutically acceptable salts thereof. Suitable monoamine oxidase inhibitors include: isocarboxazid, phenelzine, tranylcypromine and selegiline, and pharmaceutically acceptable salts thereof. Suitable reversible inhibitors of monoamine oxidase include: moclobemide, and pharmaceutically acceptable salts thereof. Suitable serotonin and noradrenaline reuptake inhibitors of use in the present invention include: venlafaxine, and pharmaceutically acceptable salts thereof.

Likewise, suitable atypical anti-depressants include: bupropion, lithium, nefazodone, trazodone and viloxazine, and pharmaceutically acceptable salts thereof. Suitable classes of anti-anxiety agent include benzodiazepines and 5-HT$_{1A}$ agonists or antagonists, especially 5-HT$_{1A}$ partial agonists, and corticotropin releasing factor (CRF) antagonists. Suitable benzodiazepines include: alprazolam, chlordiazepoxide, clonazepam, chlorazepate, diazepam, halazepam, lorazepam, oxazepam and prazepam, and pharmaceutically acceptable salts thereof. Suitable 5-HT$_{1A}$ receptor agonists or antagonists include, in particular, the 5-HT$_{1A}$ receptor partial agonists buspirone, flesinoxan, gepirone and ipsapirone, and pharmaceutically acceptable salts thereof.

For the treatment or prevention of eating disorders, including obesity, bulimia nervosa and compulsive eating disorders, a compound of the present invention may be used in conjunction with other anorectic agents. The present invention accordingly provides the use of a compound of the present invention and an anorectic agent for the manufacture of a medicament for the treatment or prevention of eating disorders. Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, orlistat, pentorex, phendimetrazine, phenmetrazine, phentermine, phenylpropanolamine, picilorex and sibutramine; and pharmaceutically acceptable salts thereof.

It will be appreciated that for the treatment or prevention of obesity, the compounds of the present invention may also be used in combination with a selective serotonin reuptake inhibitor (SSRI). The present invention accordingly provides the use of a compound of the present invention and an SSRI for the manufacture of a medicament for the treatment or prevention of obesity. Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared ($kg/m^2$), of at least 25.9. Conventionally, those persons with normal weight, have a BMI of 19.9 to less than 25.9. The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

It will be appreciated that for the treatment or prevention of pain or nociception or inflammatory diseases, a compound of the present invention may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as rofecoxib, celocoxib, etoricoxib, valdecoxib, acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

As used herein the term "mammal" includes humans and animals of economic importance such as bovine, ovine, and porcine animals, especially those that produce meat, as well as domestic animals, sports animals, zoo animals.

It will be appreciated that when using any combination described herein, both the compound of the present invention and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

Dosage

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of the conditions associated with an excess of tachykinins, a suitable dosage level of the compounds of the present invention, or pharmaceutically acceptable salts thereof, is about 0.001 to 50 mg/kg per day, in particular about 0.01 to about 25 mg/kg, such as from about 0.05 to about 10 mg/kg per day. The dosage range will generally be about 0.5 to 1000 mg per patient per day, which may be administered in single or multiple doses. Preferably, the dosage range will be about 0.5 mg to 500 mg per patient per day; more preferably about 0.5 mg to 200 mg per patient per day; and even more preferably about 5 mg to 50 mg per patient per day. Specific dosages of the compounds of the present invention, or pharmaceutically acceptable salts thereof, for administration include 1 mg, 5 mg, 10 mg, 30 mg, 100 mg, and 500 mg.

Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions for treatment or prevention of excess tachykinins comprise about 1 mg, 5 mg, 10 mg, 30 mg, 100 mg, and 500 mg of active ingredient.

Nomenclature and Abbreviations

There are several acceptable methods of naming the compounds discussed herein.

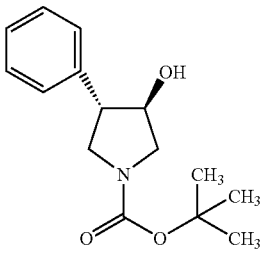

For example, the above compound can be named either as "(3R,4S) tert-butyl-3-hydroxy-4-phenylpyrrolidine-1-carboxylate" or "tert-butyl-3(R)-hydroxy-4(S)-phenylpyrrolidine-1-carboxylate".

Throughout the instant application, the following abbreviations are used with the following meanings:

| Reagents: | |
|---|---|
| CBZ-Cl | benzyl chloroformate |
| BOP | benzotriazol-1-yloxy tris(dimethylamino)phosphonium hexafluorophosphate |
| CDI | 1,1'-carbonyldiimidazole |
| MCPBA | m-chloroperbenzoic acid |
| DBU | 1,8-diazabicyclo[5.4.0]undec-7-ene |
| DCC | N,N'-dicyclohexylcarbodiimide |
| DCU | N,N'-dicyclohexylurea |
| DEAD | diethylazodicarboxylate |
| DIAD | diisopropylazodicarboxylate |
| DIBAL | diisobutylaluminum hydride |
| DIPEA | N,N-diisopropylethylamine |
| DMAP | 4-dimethylaminopyridine |
| DMF | N,N-dimethylformamide |
| DMSO | dimethylsulfoxide or methylsulfoxide |
| EDAC | 1-ethyl-3-(3-dimethylaminopropyl)carbodiimide hydrochloride |
| HBF$_4$—OMe$_2$ | tetrafluoroboric acid-dimethyl ether complex |
| HOBt | 1-hydroxybenzotriazole hydrate |
| iPr$_2$NEt | N,N-diisopropylethylamine |
| LAH | lithium aluminum hydride |
| LHMDS | lithium bis(trimethylsilyl)amide |
| MCPBA | m-chloroperbenzoic acid; 3-chloroperbenzoic acid |
| NaN$_3$ | sodium azide |
| NMM | N-methylmorpholine |
| KHMDS | potassium bis(trimethylsilyl)amide |
| NaOEt | sodium ethoxide |
| Et$_3$N | triethylamine |
| PTSA | para-toluenesulfonic acid |
| Ph$_3$P | triphenylphosphine |
| TBAF | tetra-n-butylammonium fluoride |
| TFA | trifluoroacetic acid |
| Solvents: | |
| AcOH | acetic acid |
| MeCN | acetonitrile |
| AmOH | n-amyl alcohol |
| DMSO | dimethylsulfoxide |
| DMF | N,N-dimethylformamide |
| Et$_2$O | diethyl ether |
| EtOAc | ethyl acetate |
| EtOH | ethanol |
| MeOH | methanol |
| THF | tetrahydrofuran |

| Others: | |
|---|---|
| Ac | acetyl |
| aq. | aqueous |
| Am | n-amyl |
| Ar | aryl |
| BOC | tert-butoxycarbonyl |
| Bn | benzyl |
| Bu | butyl |
| C | Celsius |
| CBZ | carbobenzyloxy (benzyloxycarbonyl) |
| calc. | calculated |
| cat. | catalytic |
| EI-MS | electron ion-mass spectroscopy |
| Et | ethyl |
| eq. | equivalent(s) |
| FAB-MS | fast atom bombardment mass spectrometry |
| g | gram(s) |
| h or hr | hour(s) |
| HPLC | high pressure liquid chromatography |
| in | inch(es) |
| iPr | isopropyl |
| MPLC | medium pressure liquid chromatography |
| Me | methyl |
| MHz | megahertz |
| min | minute(s) |
| MF | molecular formula |
| NMR | nuclear magnetic resonance |
| Ph | phenyl |
| prep. | prepared or preparative |
| Pr | propyl |
| rt | room temperature |
| R$_t$ | retention time |
| TLC | thin layer chromatography |
| TMS | tetramethylsilane |

EXAMPLES

The following examples are provided for the purpose of further illustration only and are not intended to be limitations on the disclosed invention. All $^1$H NMR spectra were performed on instrumentation at a field strength of 400 or 500 MHz.

Example 1

(3R,4S)-1-Acetyl-3-({(1R)-1-[3,5-bis(trifluoromethyl)phenyl]ethyl}oxy)-4-phenylpyrrolidine Step A: (racemic) (3R,4S) and (3S,4R) tert-Butyl-3-hydroxy-4-phenylpyrrolidine-1-carboxylate To a solution of 7 g (37.8 mmol) tert-butyl 6-oxa-3-azabicyclo[3.1.0]hexane-3-carboxylate (prepared according to the procedure of Okada, T.; Sato, S.; Tsuji. T.; Tsushima, T.; Nakai, H.; Yoshida, T.; Matsuura, S.; Chem. Pharm. Bull. 1993, 41 (1), p. 132-133) was suspended 0.36 g (1.89 mmol; 0.05 equiv.) copper(I) iodide in 100 mL dry THF under nitrogen atmosphere. The mixture was cooled in an ice/water bath. To this mixture was added dropwise 41.6 mL (41.6 mmol; 1.1 equiv.) of a 1.0M solution of phenylmagnesium bromide in THF. The reaction mixture was stirred at 0° C. for 3 hr then warmed to room temperature. The reaction mixture was poured into 150 mL sat. aq. NH$_4$Cl and stirred until a blue colored solution resulted. The mixture was transferred to a separatory funnel and extracted with diethyl ether (2×150 mL). The combined ether extracts were dried over anhydrous sodium sulfate, filtered and evaporated under vacuum. The resulting thick yellow oil was purified by silica gel chromatography eluting with hexanes/EtOAc (9/1) then hexanes/

EtOAc (1/1). The product fractions (Rf~0.5 in hexanes/EtOAc (1:1) were combined and evaporated under vacuum to give the product as a clear thick oil which solidified on standing. On larger scale this product could be further purified by crystallization from hexanes. $^1$H-NMR (CDCl$_3$): δ: 1.45 (s, 9H), 3.2-3.4 (m, 3H), 3.65-3.95 (m, 3H), 4.37 (q, 1H, 5 Hz), 7.25 (t, 3H), 7.37 (t, 2H) ppm.

Step B: (3R,4S) tert-Butyl-3-hydroxy-4-phenylpyrrolidine-1-carboxylate and (3S,4R) tert-butyl-3-hydroxy-4-phenylpyrrolidine-1-carboxylate The above racemic mixture (Step A) was purified by preparative chiral HPLC using a CHIRACEL OD column eluting with heptane/isopropanol (85/15). The fractions containing (3R,4S) tert-butyl-3-hydroxy-4-phenylpyrrolidine-1-carboxylate (analytical HPLC CHIRACEL OD, heptane/IPA (85/15), flow rate 1.0 mL/min, R$_t$ 6.99 min) and (3S,4R) tert-butyl-3-hydroxyphenylpyrrolidine-1-carboxylate (R$_t$ 7.76 min) were collected and the solvent removed under vacuum to provide the products as oils which solidified on standing. Prior to using in the next step the compound was azeotroped with benzene or toluene to remove residual water and alcohol.

Step C: (1S)-1-[3,5-bis(trifluoromethyl)phenyl]ethyl-2,2,2-trichloroethanimidoate A solution of 25.82 g (100 mmol) of (1S)-1-[3,5-bis(trifluoromethyl)phenyl]ethanol in 200 mL dry diethyl ether under nitrogen atmosphere was cooled in an ice/water bath. Neat 3 mL (20 mmol, 0.2 equiv) DBU was added to the reaction flask then the mixture was stirred at 0° C. for ten min. Slowly 15 mL (150 mmol, 1.5 equiv.) trichloroacetonitrile was added dropwise over 15 min. The reaction was stirred at 0° C. for 2 hr. during which time it became deep yellow in color. The volatiles were removed under vacuum using a cool bath (<35° C.) to give a pale brown mobile liquid which was purified by column chromatography on silica gel (3"×10" pad) in two batches eluting with hexanes/EtOAc (9/1) then hexanes/EtOAc (4/1). The product fractions were combined and the solvent removed under vacuum to give the title compound as a pale yellow oil. $^1$H-NMR (CDCl$_3$): δ: 1.74 (d, 3H, 6.5 Hz), 6.07 (q, 1H, 6.5 Hz), 7.82 (s, 1H), 7.86 (s, 2H), 8.40 (br. s, 1H) ppm.

Step D: tert-Butyl (3R,4S)-3-({(1R)-1-[3,5-bis(trifluoromethyl)phenyl]ethyl}oxy)-4-phenylpyrrolidine-1-carboxylate To a solution of 1.0 g (3.8 mmol) (3R,4S) tert-butyl-3-hydroxy-4-phenylpyrrolidine-1-carboxylate (Step B) and 3 g (7.6 mmol, 2 equiv) (S)-trichloroacetimidate (step C) in 40 mL dry heptanes and 10 mL dry methylene chloride under nitrogen atmosphere at 0° C. was added dropwise 0.092 mL (0.8 mmol, 0.2 equiv) HBF$_4$-dimethyl ether complex. The resulting reaction mixture was stirred at 0° C. for 24 hr. The volatiles were removed under vacuum and the residue dissolved in 10 mL methylene chloride and purified by column chromatography on silica gel eluting with hexanes/EtOAc (8/2) to afford a mixture of two products. This mixture was further purified by preparative HPLC on ChiralPak OD column eluting with heptanes/ethanol (98/2) to obtain the minor isomer (epimeric at the benzylic methyl position) and the title compound. $^1$H-NMR (CDCl$_3$): (rotamers): δ: 1.43-45 (2d, 3H, 6.5 Hz), 1.49-1.52 (2s, 9H), 3.3-3.5 (m, 3H), 3.73-3.97 (m, 3H), 4.53 (q, 1H, 6.5 Hz), 7.06-7.09 (m, 2H), 7.20-7.25 (m, 3H), 7.55 (m, 2H), 7.74 (s, 1H), 7.75 (s, 2H)ppm. MS: 447.9 (M-t-Bu)$^+$ observed.

Step E: (3R,4S)-3-({(1R)-1-[3,5-Bis(trifluoromethyl)phenyl]ethyl}oxy)-4-phenylpyrrolidine To a stirred solution of 315 mg product of step D in 8 mL dry methylene chloride cooled to 0° C. was added 0.5 mL anisole followed by 4 mL trifluoroacetic acid (TFA). The resulting mixture was stirred for 30 min at 0° C. then 1 hr at RT. The volatiles were removed under vacuum and the residue partitioned between 2N aq. KOH (5 mL) and methylene chloride (5 mL). The layers were separated and the aqueous layer extracted with methylene chloride (2×5 mL). The combined organic extracts were dried over sodium sulfate, filtered and solvent evaporated under vacuum to provide the title compound which was used in the next step without further purification. $^1$H-NMR (CDCl$_3$): δ: 1.43 (d, 3H, 6.5 Hz), 2.88 (dd, 1H, 8, 11.5 Hz), 3.18 (m, 3H), 3.53 (dd, 1H, 8, 11.5 Hz), 3.93 (q, 1H, 4.5 Hz), 4.53 (q, 1H, 7.5 Hz), 7.07 (d, 2H, 7.5 Hz), 7.15-7.25 (m, 3H), 7.63 (s, 2H), 7.72 (s, 1H)ppm. MS: 404.1 (MH)$^+$ observed.

Step F: (3R,4S)-1-Acetyl-3-({(1R)-1-[3,5-bis(trifluoromethyl)phenyl]ethyl}oxy)-4-phenylpyrrolidine To a solution of 200 mg intermediate step E (0.47 mmol) in 3 mL dry methylene chloride at 0° C. was added 0.097 mL pyridine (1.18 mmol) followed by 0.089 mL acetic anhydride (0.94 mmol). The reaction mixture was stirred for 6 hr at ambient temperature then the volatiles were removed under vacuum. The residue was partitioned between 2N aq. NaOH (5 mL) and methylene chloride (10 mL). The layers were separated and the aqueous layer extracted with methylene chloride (2×5 mL). The combined organic extracts were dried over sodium sulfate, filtered and solvent evaporated under vacuum. The resulting material was purified by preparative TLC eluting with methylene chloride/methanol (9/1). The resulting material was further purified by prep HPLC on Chiralpak AD column eluting with heptanes/ethanol (97/3) to afford a minor faster moving isomer A (3R,4S)-1-acetyl-3-({(1S)-1-[3,5-bis(trifluoromethyl)phenyl]ethyl}oxy)-4-phenylpyrrolidine and the title compound. $^1$H-NMR (CDCl$_3$) rotamers: δ: 1.45 (t, 3H, 6.5 Hz), 2.15 (2s, 3H) 3.38-3.63 (m, 3H), 3.85-4.03 (m, 3H), 4.58 (m, 1H), 7.1 (m, 2H), 7.25 (m, 3H), 7.61 (s, 2H), 7.78 (s, 1H)ppm. MS: 446 (MH)$^+$ observed.

Example 2

(3R,4S)-3-({(1R)-1-[3,5-Bis(trifluoromethyl)phenyl]ethyl}oxy)-4-(4-fluorophenyl)-N-methylpyrrolidine-1-carboxamide Step A: (racemic) (3R,4S) and (3S,4R) tert-Butyl-3-hydroxy-4-(4-fluorophenyl)pyrrolidine-1-carboxylate The title compound was prepared from tert-butyl 6-oxa-3-azabicyclo[3.1.0]hexane-3-carboxylate and 4-fluorophenylmagnesium bromide according to the procedure for Example 1, step A. $^1$H-NMR (CDCl$_3$): δ: 1.49 (s, 9H), 3.2-3.4 (m, 3H), 3.50 (m, 1H), 3.7-3.95 (m, 2H), 4.32 (q, 1H, 5 Hz), 7.05 (t, 2H), 7.23 (m, 2H) ppm.

Step B: (3R,4S) tert-Butyl-3-hydroxy-4-(4-fluorophenyl)pyrrolidine-1-carboxylate and (3S,4R) tert-butyl-3-hydroxy-4-(4-fluorophenyl)pyrrolidine-1-carboxylate The above racemic mixture product of Step A was purified by preparative chiral HPLC using a CHIRACEL AD column eluting with heptane/isopropanol (95/5). The fractions containing (3R,4S) tert-butyl-3-hydroxy-4-(4-fluorophenyl)pyrrolidine-1-carboxylate (analytical HPLC: heptane/isopropanol (95/5), 1 mL/min flow rate, UV detection 220 nM, (−)-CD deflection, $R_t$ 13.686 min) and (3S,4R) tert-butyl-3-hydroxy-4-(4-fluorophenyl)pyrrolidine-1-carboxylate ((+)-CD deflection, $R_t$ 16.278 min) were collected and the solvent removed under vacuum to provide the products as oils which solidified on standing. Prior to using in the next step the compound was azeotroped with benzene or toluene to remove residual water and alcohol.

Step C: tert-Butyl (3R,4S)-3-({(1R)-1-[3,5-bis(trifluoromethyl)phenyl]ethyl}oxy)-4-(4-fluorophenyl)pyrrolidine-1-carboxylate The title compound was prepared from (3R,4S) tert-butyl-3-hydroxy-4-(4-fluorophenyl)pyrrolidine-1-carboxylate (Step B, Rt 13.686 min) and (1S)-1-[3,5-bis(trifluoromethyl)phenyl]ethyl-2,2,2-trichloroethanimidoate (Example 1, step C) according to the procedure for Example 1, Step D. The product mixture was further purified by preparative HPLC on ChiralPak OD column eluting with heptanes/ethanol (98/2) to obtain the faster moving minor isomer (epimeric at the benzylic methyl position) and slower moving title compound. $^1$H-NMR (CDCl$_3$): (rotamers): δ: 1.43-47 (2d, 3H, 6.5 Hz), 1.49-1.52 (2s, 9H), 3.3-3.5 (m, 3H), 3.75-3.95 (m, 3H), 4.53 (q, 1H, 6.5 Hz), 6.95 (t, 2H), 7.05 (m, 2H), 7.53 (s, 2H), 7.76 (s, 1H)ppm. MS: 466 (M-t-Bu)$^+$ observed.

Step D: (3R,4S)-3-({(1R)-1-[3,5-Bis(trifluoromethyl)phenyl]ethyl}oxy)-4-(4-fluorophenyl)pyrrolidine The title compound was prepared from the intermediate of Step C according to the procedure for Example 1, Step E, and was used in the next step without further purification. $^1$H-NMR (CD$_3$OD): δ: 1.38 (d, 3H, 6.5 Hz), 2.74 (t, 1H, 7.5 Hz), 3.03-3.40 (m, 4H), 3.92 (q, 1H, 5.5 Hz), 4.65 (q, 1H, 6.5 Hz), 6.90 (t, 2H), 7.08 (m, 2H), 7.70 (s, 2H), 7.74 (s, 1H)ppm. MS: 422.2 (MH)$^+$ observed.

Step E: (3R,4S)-3-({(1R)-1-[3,5-Bis(trifluoromethyl)phenyl]ethyl}oxy)-4-(4-fluorophenyl)-N-methylpyrrolidine-1-carboxamide To a solution of 25 mg of the product of Step D (0.06 mmol) in 3 mL dry methylene chloride was added 0.01 mL pyridine (0.12 mmol) and 0.007 mL methylisocyanate (0.12 mmol). The resulting reaction mixture was stirred at RT for 1 hr, then the volatiles were removed under vacuum. The residue was purified by prep TLC eluting with methylene chloride/methanol (9/1) to give 25 mg of yellow glass. Further purification was achieved by prep HPLC on Chiralpak AD column eluting with heptanes/ethanol (95/5) to obtain a minor isomer A and the title compound. $^1$H-NMR (CDCl$_3$) rotamers: δ: 1.43 (d, 3H, 6.5 Hz), 2.86 (2s, 3H), 3.32-3.5 (m, 3H), 3.75-3.90 (m, 3H), 4.20 (br. s, 1H), 4.53 (q, 1H, 6.5 Hz), 6.95 (t, 2H), 7.04 (m, 2H), 7.57 (s, 2H), 7.77 (s, 1H)ppm. MS: 479.1 (MH$^+$) observed.

Example 3

3-[(3R,4S)-3-({(1R)-1-[3,5-Bis(trifluoromethyl)phenyl]ethyl}oxy)-4-(4-fluorophenyl)pyrrolidin-1-yl] cyclopent-2-en-1-one

Step A: tert-Butyl (3R,4S)-3-{[3,5-bis(trifluoromethyl)benzoyl]oxy}-4-(4-fluorophenyl)pyrrolidine-1-carboxylate To a 250 mL 3-neck round bottom flask equipped with septa, magnetic stir bar thermocouple and nitrogen line was added 5.0 g (17.77 mmol) (3R,4S) tert-butyl-3-hydroxy-4-(4-fluorophenyl)pyrrolidine-1-carboxylate (Example 2, Step B, Rt 13.686 min) and 100 mL methylene chloride. To the resulting solution was added 5.0 mL (35.54 mmol) triethylamine by syringe. The reaction mixture was cooled to 0° C. and 3.80 mL (19.55 mmol) 3,5-bis(trifluoromethyl)benzoyl chloride was added slowly by syringe over 10 min. A white precipitate formed after the addition was complete and the resulting mixture stirred for 1 hr at 0° C. when the cooling bath was removed. The reaction mixture was stirred an additional 2 hr at which time TLC (EtOAc/hex; 3:7) showed no starting material remained. The reaction mixture was poured into a separatory funnel which contained sat. aq. NaHCO$_3$. The layers were separated, the organic layer dried over anhydrous sodium sulfate, filtered and the solvent removed under vacuum to give the title compound as a yellow oil which was used without further purification in the next reaction. $^1$H-NMR (CDCl$_3$): δ: 1.55 (s, 9H), 3.4-4.09 (br. m, 6H), 5.41 (s, 1H), 7.06 (m, 2H), 7.30 (m, 2H), 8.12 (s, 1H), 8.44 (s, 2H)ppm.

Step B: tert-Butyl (3R,4S)-3-({1-[3,5-bis(trifluoromethyl)phenyl]vinyl}oxy)-4-(4-fluorophenyl)pyrrolidine-1-carboxylate In a 500 mL 3-neck round bottom flask equipped with septa, magnetic stir bar thermocouple, addition funnel and nitrogen line was placed a solution of tert-butyl (3R,4S)-3-{[3,5-bis(trifluoromethyl)benzoyl]oxy}-4-(4-fluorophenyl) pyrrolidine-1-carboxylate (product step A, 17.77 mmol) in 115 mL anhydrous THF. The solution was cooled to 0° C. with an ice/water bath. To the cooled solution was slowly added 45 mL (21.32 mmol) of a 0.5M solution of Tebbe reagent in toluene (commercially available) dropwise by addition funnel. After the addition was complete the funnel was rinsed with anhydrous toluene then THF and the resulting solution added to the reaction mixture. After stirring 1.5 h at 0° C., an additional 9.0 mL (4.5 mmol, 0.25 equiv.) of 0.5M solution of Tebbe reagent in toluene was added dropwise by addition funnel. The reaction was stirred an additional 15 min then carefully quenched by addition of 15 mL water drop by drop. The resulting mixture was transferred to a separatory funnel and extracted with ether/EtOAc. The organic layers were combined, dried over anhydrous sodium sulfate, filtered and the solvent removed under vacuum. The residue dissolved in a minimal amount of methylene chloride filtered and the solvent removed under vacuum. The resulting oil was purified by column chromatography on silica gel eluting EtOAc/hexanes gradient (5/95 to 10/90) to afford the title compound as a yellow foam. $^1$H-NMR (CDCl$_3$): δ: 1.54 (s, 9H), 3.46-4.01 (br. m, 6H), 4.0 (d, 1H), 4.61 (s, 1H), 4.91 (d, 1H), 7.08 (m, 2H), 7.22 (m, 2H), 7.83 (s, 1H), 8.0 (s, 2H)ppm.

Step C: tert-butyl (3R,4S)-3-({(1R)-1-[3,5-bis(trifluoromethyl)phenyl]ethyl}oxy)-4-(4-fluorophenyl)pyrrolidine-1-carboxylate In a 250 mL Parr pressure bottle was placed 6.8 g (13.09 mmol) tert-butyl (3R,4S)-3-({1-[3,5-bis(trifluoromethyl)phenyl]vinyl}oxy)-4-(4-fluorophenyl)pyrrolidine-1-carboxylate (step B), 70 mL ethanol followed by 1.4 g (0.2 by wt.) 10% Pd—C. The reaction mixture was shaken under 40 PSI hydrogen for 1 hr. After standing, the solution was filtered through Celite. The pad was washed with excess ethanol and the solvent of the combined filtrates removed under vacuum. to provide 6.74 g crude product which was purified by careful chromatography on silica gel eluting with EtOAc/toluene (3/97) to afford the first eluting undesired S-methyl epimer and the slower eluting desired title compound as a white semi-solid. $^1$H-NMR (CDCl$_3$): δ: 1.4-1.54 (m, 12H), 3.23-3.5 (m, 3H), 3.7-4.0 (br. m, 3H), 4.57 (br. s, 1H), 7.09 (m, 2H), 7.25 (m, 2H), 7.59 (s, 2H), 7.88 (s, 1H)ppm.

Step D: (3R,4S)-3-({(1R)-1-[3,5-Bis(trifluoromethyl)phenyl]ethyl}oxy)-4-(4-fluorophenyl)pyrrolidine hydrochloride To a solution of 1.5 g (2.876 mmol) tert-butyl (3R,4S)-3-({(1R)-1-[3,5-bis(trifluoromethyl)phenyl]ethyl}oxy)-4-(4-fluorophenyl)pyrrolidine-1-carboxylate (Step C) in 10 mL EtOAc was added 10 mL of a solution of sat. anhdr. HCl in EtOAc. The reaction mixture was a stirred at RT for 24 hr and the solvent removed under vacuum to afford a yellow oil. The resulting oil was recrystallized from ether/hexanes (3/7) to afford the title compound as a white solid (mp=107° C.). $^1$H-NMR (CD$_3$OD): δ: 1.43 (d, 3H, 6.5 Hz), 3.27 (t, 1H, 8.5 Hz), 3.44 (m, 2H), 3.73 (m, 2H), 4.20 (q, 1H, 5.5 Hz), 4.78 (q, 1H, 6.5 Hz), 7.01 (t, 2H), 7.20 (dd, 2H), 7.73 (s, 2H), 7.82 (s, 1H)ppm. MS: 422.1 (MH)$^+$ observed.

Step E: (3R,4S)-3-({(1R)-1-[3,5-Bis(trifluoromethyl)phenyl]ethyl}oxy)-4-(4-fluorophenyl)pyrrolidine The title compound was prepared from the intermediate of Step D according to the procedure for Example 1, Step E, and was used in the next step without further purification.

Step F: 3-[(3R,4S)-3-({(1R)-1-[3,5-Bis(trifluoromethyl)phenyl]ethyl}oxy)-4-(4-fluorophenyl)pyrrolidin-1-yl]cyclopent-2-en-1-one In a pressure tube was placed 562 mg cyclopentane-1,3-dione (5.73 mmol) followed by a solution of 2.3 g (3R,4S)-3-({(1R)-1-[3,5-bis(trifluoromethyl)phenyl]ethyl}oxy)-4-(4-fluorophenyl)pyrrolidine (5.46 mmol) (step E) in 12.5 mL benzene. To this solution was added 52 mg PTSA (0.027 mmol) and 4 Å bead molecular sieves (1 g). The tube was sealed and heated for 3 hr. The tube was cooled to RT and the resulting solution filtered and the solvent removed under vacuum. The resulting bright yellow oil was purified by column chromatography on silica gel eluting with EtOAc/hexanes (1/1), then EtOAc (100%), then methylene chloride/methanol (9/1). The fractions containing the desired product (as determined by TLC) were combined and the solvent removed under vacuum. The resulting yellow oil was purified by prep HPLC on Chiralcel OD eluting with heptanes/reagent alcohol (87.5/12.5) to afford the title compound as a white solid. $^1$H-NMR (CD$_3$OD) rotamers: δ: 1.43 (d, 3H, 6.5 Hz), 2.46 (m, 2H), 2.7-2.85 (m, 2H), 3.40-3.65 (m, 3H), 3.78-4.20 (m, 3H), 4.76 (quin., 1H, 6.5 Hz), 4.97, 5.03 (2s 1H), 6.98 (t, 2H), 7.18 (br. s, 2H), 7.72 (s, 2H), 7.83 (s, 1H)ppm. MS: 502.2 (MH$^+$) observed. Crystallization of 3-[(3R,4S)-3-({(1R)-1-[3,5-bis(trifluoromethyl)phenyl]ethyl}oxy)-4-(4-fluorophenyl)pyrrolidin-1-yl]cyclopent-2-en-1-one was achieved in aq. methanol (mp 45-46° C.). Alternatively, crystalline solid was obtained by crystallization in ether/hexanes mixture (mp 44-45° C.).

Example 4 tert-Butyl 4-{[(3R,4S)-3-({(1R)-1-[3,5-bis(trifluoromethyl)phenyl]ethyl}oxy)-4-phenylpyrrolidin-1-yl]carbonyl}-2,2-dimethyl-1,3-oxazolidine-3-carboxylate Step A: tert-Butyl 4-{[(3R,4S)-3-({(1R)-1-[3,5-bis(trifluoromethyl)phenyl]ethyl}oxy)-4-phenylpyrrolidin-1-yl]carbonyl}-2,2-dimethyl-1,3-oxazolidine-3-carboxylate To a solution of 38 mg (0.094 mmol) (3R,4S)-3-({(1R)-1-[3,5-bis(trifluoromethyl)phenyl]ethyl}oxy)-4-phenylpyrrolidine (Example 1. Step E) in 7.5 mL methylene chloride was added 12.7 mg (0.094 mmol) HOBT, 34.7 mg (0.14 mmol) 3-(tert-butoxycarbonyl)-2,2-dimethyl-1,3-oxazolidine-4-carboxylic acid, 0.04 mL (0.28 mmol) triethylamine and 54 mg (0.28 mmol) EDC. The resulting mixture was stirred at RT for 16 hr. The reaction mixture was partitioned between 5 mL brine and extracted with EtOAc (3×5 mL). The combined organic layers were dried over sodium sulfate, filtered and the solvent removed under vacuum. The yellow oil was purified by prep TLC eluting with methylene chloride/methanol (95/5) to give the title compound. $^1$H-NMR (CDCl$_3$) rotamers: δ: 1.4-1.8 (m, 18H), 3.20-3.70 (m, 2H), 3.88-4.3 (m, 3H), 4.43-4.70 (m, 1H), 6.97-7.10 (m, 2H), 7.20-7.35 (m, 3H), 7.53. 7.55, 7.62 (3s, 2H), 7.75, 7.78 (2s, 1H)ppm. MS: 631.3 (MH$^+$) observed.

Example 5

2-Amino-3-[(3R,4S)-3-({(1R)-1-[3,5-bis(trifluoromethyl)phenyl]ethyl}oxy)-4-phenylpyrrolidin-1-yl]-3-oxopropan-1-ol Step A: 2-Amino-3-[(3R,4S)-3-({(1R)-1-[3,5-bis(trifluoromethyl)phenyl]ethyl}oxy)-4-phenylpyrrolidin-1-yl]-3-oxopropan-1-ol To a solution of 48 mg tert-butyl 4-{[(3R,4S)-3-({(1R)-1-[3,5-bis(trifluoromethyl)phenyl]ethyl}oxy)-4-phenylpyrrolidin-1-yl]carbonyl}-2,2-dimethyl-1,3-oxazolidine-3-carboxylate (Example 4) in 3 mL methylene chloride was added 0.5 mL anisole and 3 mL TFA. The reaction mixture was stirred at RT for 2 hr and then the volatiles were removed under vacuum. The residue was partitioned between methylene chloride (5 mL) and sat. aq. sodium carbonate (5 mL). The organic layer was dried over sodium sulfate, filtered and the solvent removed under vacuum. The residue was purified by prep TLC eluting with methylene chloride/methanol (9/1) to afford the title compound. $^1$H-NMR (CDCl$_3$): δ: 1.43 (d, 3H, 6.5 Hz), 2.0 (br. s, 3H), 3.30-4.18 (m, 9H), 4.54 (m, 1H), 7.00-7.08 (m, 2H), 7.22-7.31 (m, 3H), 7.56 (s, 2H), 7.75 (s, 1H)ppm. MS: 491.2 (MH$^+$) observed.

Example 6

4-{[(3R,4S)-3-({(1R)-1-[3,5-Bis(trifluoromethyl)
phenyl]ethyl}oxy)-4-phenylpyrrolidin-1-yl]carbonyl}-1,3-oxazolidin-2-one Step A: 4-{[(3R,4S)-3-({(1R)-1-[3,5-Bis(trifluoromethyl)phenyl]ethyl}oxy)-4-phenylpyrrolidin-1-yl]carbonyl}-1,3-oxazolidin-2-one To a solution of 15 mg (0.03 mmol) 2-amino-3-[(3R,4S)-3-({(1R)-1-[3,5-bis(trifluoromethyl)phenyl]ethyl}oxy)-4-phenylpyrrolidin-1-yl]-3-oxopropan-1-ol (Example 5) in 3 mL methylene chloride was added 0.011 mL (0.08 mmol) triethylamine. The resulting mixture was cooled to 0° C. and 0.015 mL (0.03 mmol) of a 2M solution of phosgene in toluene was added by syringe. The reaction mixture was stirred at RT for 8 hr and the volatiles were removed under vacuum. The dark yellow residue was purified by prep TLC eluting with methylene chloride/methanol (95/5) to afford the title compound. $^1$H-NMR (CDCl$_3$) rotamers: δ: 1.43 (d, 3H, 6.5 Hz), 3.30-4.13 (m, 7H), 4.40-4.70 (m, 3H), 7.00-7.10 (m, 2H), 7.20-7.30 (m, 3H), 7.55 (s, 2H), 7.60 (s, 1H), 7.75, 7.77 (2s, 1H)ppm. MS: 517.0 (MH$^+$) observed.

Example 7

3-[(3R,4R)-3-({(1R)-1-[3,5-Bis(trifluoromethyl)
phenyl]ethyl}oxy)-4-(4-fluorophenyl)pyrrolidin-1-yl]cyclopent-2-en-1-one Step A: tert-Butyl (3R,4R)-3-{[3,5-bis(trifluoromethyl)benzoyl]oxy})-4-(4-fluorophenyl)pyrrolidine-1-carboxylate In a flask was placed 3.38 g (12 mmol) (3S,4R) tert-butyl-3-hydroxy-4-(4-fluorophenyl)pyrrolidine-1-carboxylate (Example 2, step B, Rt 16.278 min CHIRACEL AD column), 9.31 g (36.1 mmol) 3,5-bis(trifluoromethyl)benzoic acid, 9.45 g (36.1 mmol) triphenylphosphine. The flask was evacuated and filled with nitrogen several times. To this mixture was added 100 mL dry toluene. The resulting mixture was cooled to 0° C. then 5.7 mL (36.1 mmol) DEAD was added dropwise. After 30 min, the reaction mixture was warmed to room temperature and stirred at ambient T for 16 hr. The reaction mixture was filtered, washed with EtOAc/hexanes and the solvent of the filtrate removed under vacuum. The residue was purified by chromatography on silica gel eluting with a hexanes/EtOAc gradient (5-20-30-50% EtOAc/hexanes) to afford the title compound. NMR (CDCl$_3$): δ: 1.54 (s, 9H), 3.7-3.8 (m, 2H), 3.8-4.1 (m, 3H), 5.67 (s, 1H), 7.04 (t, 2H, 8.5 Hz), 7.31 (t, 2H, 8.5 Hz), 8.0-8.1 (m, 1H), 8.15-8.30 (m, 1H) ppm.

Step B: tert-Butyl (3R,4R)-3-({1-[3,5-bis(trifluoromethyl)phenyl]vinyl}oxy)-4-(4-fluorophenyl)pyrrolidine-1-carboxylate To a solution of 6.1 g (11.7 mmol) product of step A in 110 mL dry toluene under nitrogen atmosphere was added 7.4 g (35.2 mmol) of freshly prepared dimethyltitanocene. The reaction was heated at 80° C. for 20 hr. The volatiles were removed under vacuum and the residue purified by silica gel chromatography eluting with an EtOAc/hexanes gradient (10-30%) to afford the title compound which was used immediately in the next reaction. NMR (CDCl$_3$): δ: 1.53 (s, 9H), 3.63-4.1 (m, 5H), 4.8-4.9 (m, 2H), 7.06-7.13 (m, 2H), 7.30-7.38 (m, 2H), 7.32 (s, 2H), 7.80 (s, 1H) ppm.

Step C: tert-Butyl (3R,4R)-3-({(1R)-1-[3,5-bis(trifluoromethyl)phenyl]ethyl}oxy)-4-(4-fluorophenyl)pyrrolidine-1-carboxylate To a solution of 2.1 g (4.05 mmol) product Step B in 30 mL methanol was added 0.7 g Pd(OH)$_2$ on carbon catalyst. The reaction vessel was evacuated and hydrogen was introduced by balloon. The reaction mixture was stirred under 1 atm hydrogen for 16 hr. The mixture was filtered through Celite, rinsed with methanol and the solvent removed under vacuum. The residue was purified by silica gel chromatography eluting with hexanes/EtOAc (98/2 then 80/20 linear gradient) to afford the title compound (accompanied by a small amount of the S-methyl diastereomer). NMR (CDCl$_3$): δ: 1.40 (d, 3H, 6.5 Hz), 1.52-1.57 (m, 9H), 3.28-3.36 (m, 1H), 3.48-3.54 (m, 5H), 3.70-3.90 (m, 4H), 4.50-4.58 (m, 1H), 7.00-7.06 (m, 2H), 7.22-7.30 (m, 4H), 7.71 (s, 1H) ppm.

Step D: (3R,4R)-3-({(1R)-1-[3,5-Bis(trifluoromethyl)phenyl]ethyl}oxy)-4-(4-fluorophenyl)pyrrolidine hydrochloride To a solution of 1.36 g (2.6 mmol) product step C in EtOAc was added an equal volume of EtOAc saturated with HCl gas. The reaction mixture was stirred at RT for 1.5 hr and then the volatiles were removed under vacuum. The residue was triturated with ether to give the title compound as a solid. MS: 422 (MH$^+$).

Step E: (3R,4R)-3-({(1R)-1-[3,5-Bis(trifluoromethyl)phenyl]ethyl}-oxy)-4-(4-fluorophenyl)pyrrolidine The product of step D was partitioned between methylene chloride and sat. aq. sodium bicarbonate with shaking. The organic layer was separated, washed with brine, dried over sodium sulfate, filtered and the solvent removed under vacuum to afford the title compound which was used without further purification. NMR (CDCl$_3$): δ: 1.44 (d, 3H, 6 Hz), 3.49 (dd, 1H; 13, 3 Hz), 3.54-3.61 (m, 1H), 3.70-3.81 (m, 3H), 4.07 (t, 1H, 3.5 Hz), 4.74 (q, 1H, 6.5 Hz), 7.05 (dd, 1H; 5, 8.5 Hz), 7.34 (dd, 1H; 5, 8.5 Hz), 7.44 (m, 1H), 7.80 (s, 1H) ppm.

Step F: 3-[(3R,4R)-3-({(1R)-1-[3,5-Bis(trifluoromethyl)phenyl]ethyl}oxy)-4-(4-fluorophenyl)pyrrolidin-1-yl]cyclopent-2-en-1-one To a solution of 60 mg (0.142 mmol) product step E in 5 mL dry toluene under nitrogen atmosphere was added 21 mg (0.214 mmol) cyclopentane-1,3-dione followed by a catalytic amount of PTSA (~5 mg). The reaction mixture was heated at reflux for 16 hr. The reaction mixture was cooled to RT, diluted with methylene chloride, partitioned between sat. aq. sodium bicarbonate. The organic layer was washed with brine, dried over sodium sulfate, filtered and the solvent removed under vacuum. The residue was purified by prep TLC eluting with EtOAc (eluting 3-times) to afford the title compound. NMR (CD$_3$OD): δ: 1.36-1.41 (m, 3H), 2.45-2.55 (m, 2H), 2.75-2.95 (m, 2H), 3.45-3.7 (m, 2H), 3.7-3.8 (m, 2H), 3.85-4.15 (m, 2H), 4.76 (q, 1H, 6.5 Hz), 5.07-5.10 (m, 1H), 7.06 (dd, 2H; 2, 9 Hz), 7.37 (dd, 1H; 5.5, 9 Hz), 7.45 (s, 2H), 7.78 (s, 1H) ppm. MS: 502 (M+H).

Example 8

(5R)-3-[(3R,4S)-3-({(1R)-1-[3,5-Bis(trifluoromethyl)phenyl]ethyl}oxy)-4-(4-fluorophenyl)pyrrolidin-1-yl]-5-methylcyclopent-2-en-1-one and (5S)-3-[(3R,4S)-3-({(1R)-1-[3,5-Bis(trifluoromethyl)phenyl]ethyl}oxy)-4-(4-fluorophenyl)pyrrolidin-1-yl]-5-methylcyclopent-2-en-1-one Step A: (5R)-3-[(3R,4S)-3-({(1R)-1-[3,5-Bis(trifluoromethyl)phenyl]ethyl}oxy)-4-(4-fluorophenyl)pyrrolidin-1-yl]-5-methylcyclopent-2-en-1-one and (5S)-3-[(3R,4S)-3-({(1R)-1-[3,5-Bis(trifluoromethyl)phenyl]ethyl}oxy)-4-(4-fluorophenyl)pyrrolidin-1-yl]-5-methylcyclopent-2-en-1-one In a round bottomed flask, 40 mg (0.07977 mmol) 3-[(3R,4S)-3-({(1R)-1-[3,5-bis(trifluoromethyl)phenyl]ethyl}oxy)-4-(4-fluorophenyl)pyrrolidin-1-yl]cyclopent-2-en-1-one (Example 3, step F) was azeotroped with tetrahydrofuran (twice). The flask was stored under nitrogen atmosphere and the material dissolved in tetrahydrofuran (2.5 mL) and cooled to −78° C. To this solution was added by syringe, 0.067 mL (1.25 equiv, 0.0997 mmol) of a 1.5M solution of LDA. The resulting yellow solution was stirred for 1 hr at −78° C. then 0.2 mL HMPA was added by syringe. After 5 minutes 0.124 mL (0.199 mmol) iodomethane was added by syringe. The resulting yellow solution was stirred for 4 hr at −78° C. then quenched by the addition of 1 mL water. The resulting mixture was warmed to RT acidified to pH<3 with 2N aq. HCl and extracted with EtOAc (3×5 mL). The combined organic extracts were dried over anhydrous sodium sulfate, filtered and the solvent removed under vacuum to provide 40 mg of a yellow oil. The resulting oil was purified by prep TLC on silica gel eluting with methylene chloride/methanol (95/5). The UV active band with Rf~0.5 was isolated. The resulting yellow oil was purified by prep HPLC on Chiralcel AD eluting with heptanes/reagent alcohol (93.5/6.5) to afford diastereomer A and diastereomer B (absolute stereochemistry of each methyl isomer was not assigned). Isomer A, $^1$H-NMR (CD$_3$OD) rotamers δ: 1.17, 1.21 (2d, 3H), 1.43 (d, 3H, 6.5 Hz), 2.52 (m, 1H), 2.83 (dd, 1H), 3.04 (m, 1H), 3.37-4.20 (m, 6H), 4.73 (m, 1H), 4.88, 4.96 (2s, 1H), 6.90-7.02 (m, 2H), 7.12-7.20 (m, 2H), 7.67 (s, 2H), 7.80 (s, 1H)ppm. Isomer B, $^1$H-NMR (CD$_3$OD) rotamers: δ: 1.10 (2d, 3H), 1.42 (d, 3H, 6.5 Hz), 2.37 (t, 1H), 2.51 (m, 1H), 3.00 (m, 1H), 3.36-3.60 (m, 3H), 3.74-4.20 (m, 3H), 4.23 (q, 1H, 6.5 Hz), 4.90, 4.97 (2s, 1H), 6.92-7.01 (m, 2H), 7.13-7.20 (m, 2H), 7.65 (s, 1H), 7.66 (s, 1H), 7.81 (s, 1H)ppm. MS: 516.2 (MH$^+$) observed for both compounds.

Example 9

(5R)-3-[(3R,4S)-3-({(1R)-1-[3,5-Bis(trifluoromethyl)phenyl]ethyl}oxy)-4-(4-fluorophenyl)pyrrolidin-1-yl]-5-hydroxycyclopent-2-en-1-one and (5S)-3-[(3R,4S)-3-({(1R)-1-[3,5-Bis(trifluoromethyl)phenyl]ethyl}oxy)-4-(4-fluorophenyl)pyrrolidin-1-yl]-5-hydroxycyclopent-2-en-1-one Step A: (5R)-3-[(3R,4S)-3-({(1R)-1-[3,5-Bis(trifluoromethyl)phenyl]ethyl}oxy)-4-(4-fluorophenyl)pyrrolidin-1-yl]-5-hydroxycyclopent-2-en-1-one and (5S)-3-[(3R,4S)-3-({(1R)-1-[3,5-Bis(trifluoromethyl)phenyl]ethyl}oxy)-4-(4-fluorophenyl)pyrrolidin-1-yl]-5-hydroxycyclopent-2-en-1-one In a round bottomed flask, 20 mg (0.0399 mmol) 3-[(3R,4S)-3-({(1R)-1-[3,5-bis(trifluoromethyl)phenyl]ethyl}oxy)-4-(4-fluorophenyl)pyrrolidin-1-yl]cyclopent-2-en-1-one (Example 3, step F) was dissolved in tetrahydrofuran (1 mL) under nitrogen atmosphere and cooled to −78° C. To this solution was added by syringe, 0.024 mL (1.2 equiv, 0.0479 mmol) of a 2M solution of LDA in heptanes/THF. The resulting yellow solution was stirred for 1 hr at −78° C. then a solution of 34.7 mg (0.0798 mmol) MoOPH in 1 mL THF was added by syringe. The resulting deep yellow solution was stirred for 1 hr at −78° C. then stirred at 0° C. to RT for 10 min. and quenched by the addition of sat. aq. Na$_2$SO$_3$. The resulting mixture was stirred 10 min. then extracted with EtOAc (2×10 mL). The combined organic extracts were dried over anhydrous sodium sulfate, filtered and the solvent removed under vacuum. The resulting oil was purified by prep TLC on silica gel eluting with methylene chloride/methanol (9/1). The UV active band with Rf~0.4 was isolated. The resulting yellow oil was purified by prep HPLC on Chiralcel OD eluting with heptanes/reagent alcohol (77.5/22.5) to afford diastereomer A and diastereomer B (absolute stereochemistry of each hydroxy isomer was not assigned). Isomer A, $^1$H-NMR (CD$_3$OD) rotamers δ: 1.42 (d, 3H, 6.5 Hz), 2.50 (m, 1H), 3.18 (m, 1H), 3.30-4.30 (m, 6H), 4.66-4.90 (m, 2H), 4.93, 4.98 (2s, 1H), 6.90-7.00 (t, 2H), 7.10-7.20 (m, 2H), 7.67 (s, 2H), 7.80 (s, 1H)ppm. Isomer B, $^1$H-NMR (CD$_3$OD) rotamers: δ: 1.41 (d, 3H, 6.5 Hz), 2.53 (t, 1H), 3.13 (m, 1H), 3.30-4.30 (m, 6H), 4.75-4.85 (m, 2H), 4.90, 4.97 (2s, 1H), 6.96 (t, 2H), 7.17 (t, 2H), 7.66 (s, 1H), 7.66 (s, 1H), 7.79 (s, 1H)ppm. MS: 516.2 (MH$^+$) observed for both compounds.

Example 10

3-[(3R,4S)-3-({(1R)-1-[3,5-Bis(trifluoromethyl)phenyl]ethyl}oxy)-4-(4-fluorophenyl)pyrrolidin-1-yl]-4-methylcyclopent-2-en-1-one Step A: 3-[(3R,4S)-3-({(1R)-1-[3,5-Bis(trifluoromethyl)phenyl]ethyl}oxy)-4-(4-fluorophenyl)pyrrolidin-1-yl]-4-methylcyclopent-2-en-1-one In a round bottomed flask, 50 mg (0.0997 mmol) 3-[(3R,4S)-3-({(1R)-1-[3,5-bis(trifluoromethyl)phenyl]ethyl}oxy)-4-(4-fluorophenyl)pyrrolidin-1-yl]cyclopent-2-en-1-one (Example 3, step F) was dissolved in tetrahydrofuran (5 mL) under nitrogen atmosphere and cooled to −78° C. To this solution was added by syringe, 0.090 mL (0.9 equiv, 0.0897 mmol) of a 1M solution of LiHMDS in THF. The resulting faint yellow solution was stirred for 1 hr at −78° C. then 0.0155 mL (0.249 mmol) iodomethane was added by syringe. The resulting yellow solution was stirred for 5 min at −78° C. then warmed to RT over 30 min. The reaction was quenched by the addition of 2 mL sat. aq. NH$_4$Cl stirred 5 min then 2 mL water was added. The resulting mixture was extracted with ether (3×10 mL). The combined organic extracts were dried over anhydrous sodium sulfate, filtered and the solvent removed under vacuum to provide a yellow oil. The resulting oil was purified by prep TLC on silica gel eluting with methylene chloride/methanol (9/1). The UV active band with Rf~0.85 was isolated. The resulting yellow oil (48 mg) was purified by prep HPLC on Chiralcel OD eluting with heptanes/absolute alcohol (94/6) to afford the title compound as a mixture of stereoisomers. $^1$H-NMR (CD$_3$OD) rotamers: δ: 1.2-1.45 (m, 6H), 2.04 (m, 1H), 2.78 (m, 1H), 3.18 (m, 1H), 3.30-4.35 (m, 6H), 4.7-4.9 (m, 2H), 4.95, 5.0 (2d, 1H), 6.95-7.02 (m, 2H), 7.10-7.22 (m, 2H), 7.62 (s, 1H), 7.80 (s, 1H), 7.83 (s, 1H)ppm. MS: 516.2 (MH$^+$) observed.

Example 11

(4R)-3-[(3R,4S)-3-({(1R)-1-[3,5-Bis(trifluoromethyl)phenyl]ethyl}oxy)-4-(4-fluorophenyl)pyrrolidin-1-yl]-4-hydroxycyclopent-2-en-1-one and (4S)-3-[(3R,4S)-3-({(1R)-1-[3,5-Bis(trifluoromethyl)phenyl]ethyl}oxy)-4-(4-fluorophenyl)pyrrolidin-1-yl]-4-hydroxycyclopent-2-en-1-one Step A: (4R)-3-[(3R,4S)-3-({(1R)-1-[3,5-Bis(trifluoromethyl)phenyl]ethyl}oxy)-4-(4-fluorophenyl)pyrrolidin-1-yl]-4-hydroxycyclopent-2-en-1-one and (4S)-3-[(3R,4S)-3-({(1R)-1-[3,5-Bis(trifluoromethyl)phenyl]ethyl}oxy)-4-(4-fluorophenyl)pyrrolidin-1-yl]-4-hydroxycyclopent-2-en-1-one In a round bottomed flask, 250 mg (0.4985 mmol) 3-[(3R,4S)-3-({(1R)-1-[3,5-bis(trifluoromethyl)phenyl]ethyl}oxy)-4-(4-fluorophenyl)pyrrolidin-1-yl]cyclopent-2-en-1-one (Example 3, step F) was dissolved in tetrahydrofuran (5 mL) under nitrogen atmosphere and cooled to −78° C. To this solution was added by syringe, 0.450 mL (0.9 equiv., 0.4487 mmol) of a 1M solution of LiHMDS in THF. The resulting faint yellow solution was stirred for 1 hr at −78° C. then 433 mg (0.9971 mmol)) solid MoOPh was added. The resulting yellow solution was stirred for 5 min at −78° C. then warmed to RT. After 45 min. The reaction was quenched by the addition of 3 mL sat. aq. $Na_2SO_3$, stirred 5 min then extracted with methylene chloride (3×10 mL). The combined organic extracts were dried over anhydrous sodium sulfate, filtered and the solvent removed under vacuum to provide a yellow oil. The resulting oil was purified by prep TLC on silica gel eluting with methylene chloride/methanol (9/1). The UV active band was isolated. The resulting yellow oil (118 mg) was purified by prep HPLC on Chiralcel OD eluting with heptanes/absolute alcohol (87.5/12.5) to afford isomer A of the title compound and isomer B of the title compounds (absolute stereochemistry at the 4-position was not assigned). Isomer A, $^1$H-NMR ($CD_3OD$) rotamers δ: 1.43 (m, 3H), 2.28 (dd, 1H), 2.81 (m, 1H), 2.95 (m, 2H), 3.65 (m, 1H), 3.83 (m, 1H), 4.13 (m, 1H), 4.45 (m, 1H), 4.78 (m, 1H), 4.98 (m, 2H), 6.96 (d, 2H, 8.5 Hz), 7.13 (m, 2H), 7.73 (s, 1H), 7.77 (s, 1H), 7.82 (s, 1H)ppm. Isomer B, $^1$H-NMR ($CD_3OD$) rotamers: δ: 1.43 (m, 3H), 2.28 (m, 1H), 2.80 (m, 1H), 3.20-3.55 (m, 2H), 3.55-4.23 (m, 3H), 4.60-5.0 (m, 3H), 6.98 (t, 2H, 8.5 Hz), 7.17 (m, 2H), 7.65 (s, 1H), 7.70 (s, 1H), 7.81 (s, 1H)ppm. MS: 518.2 (MH$^+$) observed for both compounds.

Example 12

2-{2-[(3R,4S)-3-({(1R)-1-[3,5-Bis(trifluoromethyl)phenyl]ethyl}oxy)-4-(4-fluorophenyl)pyrrolidin-1-yl]-5-oxocyclopent-1-en-1-yl}acetamide Step A: 3-[(3R,4S)-3-({(1R)-1-[3,5-Bis(trifluoromethyl)phenyl]ethyl}oxy)-4-(4-fluorophenyl)pyrrolidin-1-yl]-2-[(dimethylamino)methyl]cyclopent-2-en-1-one In a pressure tube, 50 mg (0.0997 mmol) 3-[(3R,4S)-3-({(1R)-1-[3,5-bis(trifluoromethyl)phenyl]ethyl}oxy)-4-(4-fluorophenyl)pyrrolidin-1-yl]cyclopent-2-en-1-one (Example 3, step F), 10.5 mg (0.3489 mmol) paraformaldehyde, and 20.3 mg (0.2493 mmol) dimethylamine hydrochloride was dissolved in ethanol (4 mL). The tube was sealed and heated in an oil bath for 3 hr at 90° C. The reaction mixture was cooled to RT, the tube was opened and the solvent removed under vacuum. The residue was partitioned between of 5 mL 1N aq. NaOH and EtOAc (3×5 mL). The combined organic extracts were dried over anhydrous sodium sulfate, filtered and the solvent removed under vacuum to provide a yellow oil. The resulting oil was purified by prep TLC on silica gel eluting with methylene chloride/methanol (9/1). The more polar UV active band was isolated to afford the title compound as a glassy yellow solid. $^1$H-NMR ($CD_3OD$) rotamers: δ: 1.44 (d, 3H, 6.5 Hz), 2.4-2.90 (m, 10H), 3.4-4.6 (m, 8H), 4.82 (br. s, 1H), 6.97 (t, 2H, 8.5 Hz), 7.23 (br. s, 2H), 7.69 (s, 2H), 7.80 (s, 1H)ppm. MS: 559.1 (MH$^+$) observed.

Step B: {2-[(3R,4S)-3-({(1R)-1-[3,5-Bis(trifluoromethyl)phenyl]ethyl}oxy)-4-(4-fluorophenyl)pyrrolidin-1-yl]-5-oxocyclopent-1-en-1-yl}-N,N,N-trimethylmethanaminium iodide In a pressure tube, 22 mg (0.0394 mmol) 3-[(3R,4S)-3-({(1R)-1-[3,5-bis(trifluoromethyl)phenyl]ethyl}oxy)-4-(4-fluorophenyl)pyrrolidin-1-yl]-2-[(dimethylamino)methyl]cyclopent-2-en-1-one (step A), and 0.025 mL (0.3939 mmol) iodomethane was dissolved in benzene (1 mL). The tube was sealed and heated in an oil bath for 2.5 hr at ~60° C. The reaction mixture was cooled to RT, the tube was opened and the solvent removed under vacuum to afford the title compound as a yellow oil which was used in the next reaction without further purification.

Step C: {2-[(3R,4S)-3-({(1R)-1-[3,5-Bis(trifluoromethyl)phenyl]ethyl}oxy)-4-(4-fluorophenyl)pyrrolidin-1-yl]-5-oxocyclopent-1-en-1-yl}acetonitrile A solution of 32 mg (0.0394 mmol) {2-[(3R,4S)-3-({(1R)-1-[3,5-Bis(trifluoromethyl)phenyl]ethyl}oxy)-4-(4-fluorophenyl)pyrrolidin-1-yl]-5-oxocyclopent-1-en-1-yl}-N,N,N-trimethylmethanaminium iodide (step B) and 41.7 mg (0.8505 mmol) sodium cyanide in 95% ethanol (5 mL) was refluxed for 6 hr. The reaction mixture was cooled to RT and the solvent removed under vacuum. The residue was purified by prep TLC on silica gel eluting with methylene chloride/methanol (9/1). The UV active band ($R_f$~0.4) was isolated to afford the title compound as a glassy yellow solid. $^1$H-NMR ($CD_3OD$): δ: 1.45 (d, 3H, 6.5 Hz), 2.43 (br. s, 2H), 2.79 (br. s, 2H), 3.4-4.55 (m, 8H), 4.79 (q, 1H, 6.5 Hz), 6.99 (t, 2H, 8.5 Hz), 7.20 (m, 2H), 7.72 (s, 2H), 7.83 (s, 1H)ppm. MS: 541.0 (MH$^+$) observed.

Step D: 2-{2-[(3R,4S)-3-({(1R)-1-[3,5-bis(trifluoromethyl)phenyl]ethyl}oxy)-4-(4-fluorophenyl)pyrrolidin-1-yl]-5-oxocyclopent-1-en-1-yl}acetamide To a solution of 5.8 mg (0.0107 mmol) {2-[(3R,4S)-3-({(1R)-1-[3,5-Bis(trifluoromethyl)phenyl]ethyl}oxy)-4-(4-fluorophenyl)pyrrolidin-1-yl]-5-oxocyclopent-1-en-1-yl}acetonitrile (step C) in 5 drops DMSO was added 10 mg (0.072 mmol) potassium carbonate and 5 drops 30% aq. hydrogen peroxide. The reaction mixture was stirred at RT for 4 h, then the volatiles removed overnight using a nitrogen gas stream. The residue was purified by prep TLC on silica gel eluting with methylene chloride/methanol (9/1). The UV active band (~$R_f$~0.7) was isolated to afford the title compound as a glassy clear solid. $^1$H-NMR ($CD_3OD$): δ: 1.44 (d, 3H, 6.5 Hz), 2.43 (br. s, 2H), 2.76 (br. s, 2H), 3.3-4.45 (m, 8H), 4.77 (q, 1H, 6.5 Hz), 6.98 (t, 2H, 8.5 Hz), 7.18 (m, 2H), 7.72 (s, 2H), 7.83 (s, 1H)ppm. MS: 559.1 (M+H) observed.

Example 13

Methyl 2-[(3R,4S)-3-({(1R)-1-[3,5-bis(trifluoromethyl)phenyl]ethyl}oxy)-4-(4-fluorophenyl)pyrrolidin-1-yl]-5-oxocyclopent-1-ene-1-carboxylate Step A: 3-[(3R,4S)-3-({(1R)-1-[3,5-Bis(trifluoromethyl)phenyl]ethyl}oxy)-4-(4-fluorophenyl)pyrrolidin-1-yl]-2-bromocyclopent-2-en-1-one In a round bottomed flask, 150 mg (0.299 mmol) 3-[(3R,4S)-3-({(1R)-1-[3,5-bis(trifluoromethyl)phenyl]ethyl}oxy)-4-(4-fluorophenyl)pyrrolidin-1-yl]cyclopent-2-en-1-one (Example 3, step F) was dissolved in methylene chloride (5 mL) under nitrogen atmosphere and cooled to 0° C. To this solution was added a solution of 300 mg (1.877 mmol) bromine in methylene chloride (5 mL). The resulting solution was stirred for 0.25 hr at 0° C. then was quenched by the addition of sat. aq. $Na_2SO_3$ until a clear solution resulted. The mixture was diluted with 5 mL water then extracted with methylene chloride (3×5 mL). The combined organic extracts were dried over anhydrous sodium sulfate, filtered and the solvent removed under vacuum. The resulting oil was purified by prep TLC on silica gel eluting with methylene chloride/methanol (95/5) to afford the title compound and a small amount of the less polar 2,2-dibromo compound. Monobromide, $^1$H-NMR ($CD_3OD$): δ: 1.44 (d, 3H), 2.48 (br. s, 2H), 2.87 (m, 2H), 3.43 (m, 1H), 3.66 (m, 1H), 4.0-4.22 (m, 2H), 4.70-4.83 (m, 2H), 6.98 (t, 2H), 7.18 (dd, 2H), 7.70 (s, 2H), 7.83 (s, 1H)ppm. MS: 580.0 and 582 ($MH^+$) observed. Dibromide, $^1$H-NMR ($CD_3OD$): δ: 1.46 (d, 3H), 2.82 (d, 1H), 3.24 (dd, 1H), 3.38-4.85 (m, 7H), 5.35, 5.36 (2s, 1H), 7.00 (m, 2H), 7.20 (m, 2H), 7.67-7.87 (m, 3H)ppm. MS: 657.9, 659.9 and 661.9 ($MH^+$) observed.

Step B: Methyl 2-[(3R,4S)-3-({(1R)-1-[3,5-bis(trifluoromethyl)phenyl]ethyl}oxy)-4-(4-fluorophenyl)pyrrolidin-1-yl]-5-oxocyclopent-1-ene-1-carboxylate In a round bottomed flask, 50 mg (0.0862 mmol) 3-[(3R,4S)-3-({(1R)-1-[3,5-bis(trifluoromethyl)phenyl]ethyl}oxy)-4-(4-fluorophenyl)pyrrolidin-1-yl]-2-bromocyclopent-2-en-1-one (Example 14, step A) was dissolved in 10 mL methanol. To the solution was added 0.25 mL triethylamine. The solution was degassed and purged with nitrogen several times. To the solution was added 15 mg (0.0129 mmol) tetrakis(triphenylphosphine)Pd(0)-catalyst. The flask was equipped with a reflux condensor and a carbon monoxide balloon. The reaction mixture was degassed and purged with CO several times then heated at reflux under CO atmosphere for 16 hr. The reaction was cooled to RT and the volatiles removed under vacuum. The residue was dissolved in 5 mL methylene chloride, filtered through filter aid and the solvent removed under vacuum to provide a brown oil. The resulting oil was purified by prep TLC on silica gel eluting with methylene chloride/methanol (9/1). The product band, $R_f$~0.6, was isolated to afford the title compound as an oil. $^1$H-NMR ($CD_3OD$): δ: 1.43 (t, 3H), 2.44 (m, 1H), 2.48 (t, 1H), 2.80 (t, 1H), 2.87 (q, 1H), 3.65-3.90 (m, 3H), 3.67, 3.82 (2s, 3H), 4.05-4.22 (m, 2H), 4.72 (m, 1H), 6.97 (t, 2H), 7.17 (m, 2H), 7.68 (s, 2H), 7.80, 7.81 (2s, 1H)ppm. MS: 559.9 ($MH^+$) observed.

Example 14

2-[(3R,4S)-3-({(1R)-1-[3,5-Bis(trifluoromethyl)phenyl]ethyl}oxy)-4-(4-fluorophenyl)pyrrolidin-1-yl]-N-methyl-5-oxocyclopent-1-ene-1-carboxamide Step A: 2-[(3R,4S)-3-({(1R)-1-[3,5-Bis(trifluoromethyl)phenyl]ethyl}oxy)-4-(4-fluorophenyl)pyrrolidin-1-yl]-N-methyl-5-oxocyclopent-1-ene-1-carboxamide In a round bottomed flask, 85 mg (0.146 mmol) 3-[(3R,4S)-3-({(1R)-1-[3,5-bis(trifluoromethyl)phenyl]ethyl}oxy)-4-(4-fluorophenyl)pyrrolidin-1-yl]-2-bromocyclopent-2-en-1-one (Example 14, step A) was dissolved in 6 mL of a 2.0M solution of methylamine in THF. To the solution was added 45 mg (0.038 mmol) tetrakis(triphenylphosphine)Pd(0) catalyst. The flask was equipped with a reflux condensor and a carbon monoxide balloon. The reaction mixture was degassed and purged with CO several times then heated at reflux under CO atmosphere for 16 hr. The reaction was cooled to RT, filtered through filter aid and the solvent removed under vacuum to provide a brown oil. The resulting oil was purified by prep TLC on silica gel eluting with methylene chloride/methanol (9/1). The product band, $R_f$~0.5, was isolated to afford the title compound as an pale yellow oil. $^1$H-NMR ($CD_3OD$): δ: 1.43 (t, 3H, 6.5 Hz), 2.47 (m, 2H), 2.75-2.90 (m, 5H), 3.47 (m, 1H), 3.75 (m, 1H), 3.90-4.25 (m, 3H), 4.74 (m, 1H), 6.97 (q, 2H), 7.19 (m, 2H), 7.68 (s, 2H), 7.83 (s, 1H)ppm. MS: 559.1 ($MH^+$) observed.

Using the procedures comparable to those described above the compounds of the following Examples were prepared.

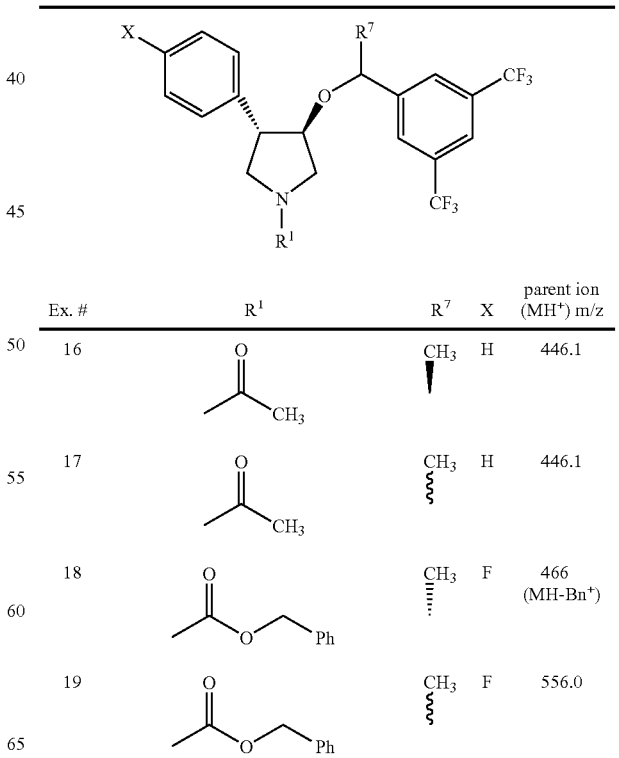

| Ex. # | R$^1$ | R$^7$ | X | parent ion ($MH^+$) m/z |
|---|---|---|---|---|
| 16 | ![acetyl] O, CH₃, CH₃ | CH₃ | H | 446.1 |
| 17 | ![acetyl] O, CH₃, CH₃ | CH₃ | H | 446.1 |
| 18 | ![Cbz] O, O, Ph | CH₃ | F | 466 (MH-Bn$^+$) |
| 19 | ![Cbz] O, O, Ph | CH₃ | F | 556.0 |

| Ex. # | R¹ | R⁷ | X | parent ion (MH⁺) m/z |
|---|---|---|---|---|
| 20 | acetyl (COCH₃) | CH₃ (wavy) | F | 464.0 |
| 21 | acetyl (COCH₃) | CH₃ (wedge) | F | 464.0 |
| 22 | acetyl (COCH₃) | CH₃ (dashed) | F | 464.0 |
| 23 | COCH₂NHCH₃ | CH₃ (wavy) | F | 479.1 |
| 24 | COCH₂NHCH₃ | CH₃ (wedge) | F | 479.1 |
| 25 | COCH₂N(CH₃)₂ | CH₃ (wavy) | F | 493.1 |
| 26 | COCH₂N(CH₃)₂ | CH₃ (wedge) | F | 493.1 |
| 27 | COCH₂N(CH₃)₂ | CH₃ (dashed) | F | 493.1 |
| 28 | COOC(CH₃)₃ | CH₃ (dashed) | H | 447.9 (MH⁺)-56 |
| 29 | COOC(CH₃)₃ | CH₃ (wedge) | H | 447.9 (MH⁺)-56 |
| 30 | CO-morpholine | CH₃ (dashed) | H | 517.0 |
| 31 | COC(CH₃)₃ | CH₃ (dashed) | H | 488.0 |
| 32 | COC(CH₃)₂CH₂OH | CH₃ (dashed) | H | 490.1 |
| 33 | COCH₂NHCH₃ | CH₃ (dashed) | H | 461.0 |
| 34 | COCH₂NHCH₃ | CH₃ (wedge) | H | 461.0 |
| 35 | COCH₂OH | CH₃ (wedge) | H | 462.1 |
| 36 | COCH₂OH | CH₃ (dashed) | H | 462.1 |
| 37 | CO-(5-oxopyrrolidin-2-yl) | CH₃ (wedge) | H | 515.1 |
| 38 | CO-(5-oxopyrrolidin-2-yl) | CH₃ (dashed) | H | 515.1 |
| 39 | CO-(5-oxopyrrolidin-2-yl) | CH₃ (wedge) | F | 533.1 |

-continued

[Structure: X-phenyl attached to pyrrolidine (with N-R¹) bearing O-CH(R⁷)-3,5-bis(trifluoromethyl)phenyl group]

| Ex. # | R¹ | R⁷ | X | parent ion (MH⁺) m/z |
|---|---|---|---|---|
| 40 | (S)-5-oxopyrrolidin-2-yl carbonyl (acetyl on pyroglutamate) | CH₃ | F | 533.1 |
| 41 | 1-acetylpiperidin-4-yl carbonyl | CH₃ | F | 575.1 |
| 42 | 1-acetylpiperidin-4-yl carbonyl | CH₃ | F | 575.1 |
| 43 | 1-acetylpiperidin-4-yl carbonyl | CH₃ | F | 575.1 |
| 44 | CH₃C(O)N(NHEt) (acetyl ethylhydrazide) | CH₃ | F | 493.1 |
| 45 | CH₃C(O)NH-C(CH₃)₃ | CH₃ | F | 521.0 |
| 46 | CH₃C(O)NH-CH(CH₃)₂ | CH₃ | F | 507.0 |
| 47 | CH₃C(O)N(NHEt) | CH₃ | F | 493.0 |
| 48 | CH₃C(O)NH-C(CH₃)₃ | CH₃ | F | 521.0 |
| 49 | CH₃C(O)NH-CH(CH₃)₂ | CH₃ | F | 507.0 |
| 50 | CH₃C(O)CH₂CH₃ | CH₃ | F | 478.1 |
| 51 | CH₃C(O)CH₂CH₃ | CH₃ | F | 478.1 |
| 52 | CH₃C(O)CH(CH₃)₂ | CH₃ | F | 492.0 |
| 53 | CH₃C(O)CH(CH₃)₂ | CH₃ | F | 492.0 |
| 54 | (S)-5-oxopyrrolidin-2-yl carbonyl | CH₃ | F | 533.0 |
| 55 | (S)-5-oxopyrrolidin-2-yl carbonyl | CH₃ | F | 533.0 |
| 56 | 1-methyl-5-oxopyrrolidin-2-yl carbonyl | CH₃ | F | 547.1 |
| 57 | 1-methyl-5-oxopyrrolidin-2-yl carbonyl | CH₃ | F | 547.1 |
| 58 | H | CH₃ | H | 404.2 |
| 59 | CH₃C(O)H (acetaldehyde / formyl acetyl) | CH₃ | F | 450.1 |

-continued

| Ex. # | R¹ | R⁷ | X | parent ion (MH⁺) m/z |
|---|---|---|---|---|
| 60 | acetaldehyde (CH₃CHO) | CH₃ | F | 450.1 |
| 61 | (S)-1-methyl-5-oxopyrrolidin-2-yl methyl ketone | CH₃ | F | 547.1 |
| 62 | (R)-1-methyl-5-oxopyrrolidin-2-yl methyl ketone | CH₃ | F | 547.1 |
| 63 | 1-(5-methylpyrazin-2-yl)ethanone | CH₃ | F | 542.1 |
| 64 | 1-(5-methylpyrazin-2-yl)ethanone | CH₃ | F | 542.0 |
| 65 | 3-methylcyclopent-2-enone | CH₃ | F | 502.2 |
| 66 | 1,4-diacetylpiperazine | CH₃ | F | 576.1 |
| 67 | 1,4-diacetylpiperazine | CH₃ | F | 576.1 |
| 68 | 7-acetyl-3-(trifluoromethyl)-5,6,7,8-tetrahydro-[1,2,4]triazolo[4,3-a]pyrazine | CH₃ | F | 640.0 |
| 69 | N-((5-methyl-4H-1,2,4-triazol-3-yl)methyl)acetamide | CH₃ | F | 559.8 |
| 70 | N-((1H-1,2,3-triazol-4-yl)methyl)acetamide | CH₃ | F | 549 observed |
| 71 | N-(1-(4H-1,2,4-triazol-3-yl)ethyl)acetamide | CH₃ | F | 559.9 |
| 72 | 4-acetyl-3-Boc-2,2-dimethyloxazolidine | CH₃ | F | 649.2 |
| 73 | N-ethyl-N-aminoacetamide | CH₃ | H | 475.2 |
| 74 | N-isopropylacetamide | CH₃ | H | 489.2 |
| 75 | 3-amino-4-hydroxybutan-2-one | CH₃ | F | 509.2 |
| 76 | 4-acetyloxazolidin-2-one | CH₃ | F | 534.9 |
| 77 | 3-methylcyclopent-2-enone | CH₃ | H | 484.2 |
| 78 | 4-acetylimidazolidin-2-one | CH₃ | F | 534.1 |

-continued

[Structure: 4-(X-phenyl)-3-[(1-(3,5-bis(trifluoromethyl)phenyl)-R7)methoxy]pyrrolidine with N-R1]

| Ex. # | R1 | R7 | X | parent ion (MH+) m/z |
|---|---|---|---|---|
| 79 | 1-(3,5-bis(trifluoromethyl)phenyl)ethyl acetate | CH3 | F | 466.1 observed |
| 80 | 3-methylcyclohex-2-enone | CH3 | H | 498.3 |
| 81 | H | CH3 | F | 422.1 |
| 82 | H | CH3 | F | 422.1 |
| 83 | 2,3-dimethylcyclopent-2-enone | CH3 | H | 628.2 |
| 84 | 2,3-dimethylcyclopent-2-enone | CH3 | H | 498.0 |
| 85 | 3,6,6-trimethylcyclohex-2-enone | CH3 | H | 526.2 |
| 86 | 3,5,5-trimethylcyclohex-2-enone | CH3 | H | 526.2 |
| 87 | 2,3-dimethylcyclopent-2-enone | CH3 | F | 516.2 |
| 88 | 3-methylcyclobut-2-enone | CH3 | H | 470.1 |

-continued

| Ex. # | R1 | R7 | X | parent ion (MH+) m/z |
|---|---|---|---|---|
| 89 | 2-hydroxy-2,4-dimethylcyclopent-3-enone | CH3 | F | 532.1 |
| 90 | 4-methyl-2(5H)-furanone | CH3 | H | 486.2 |
| 91 | 1,4-dimethyl-3-pyrrolin-2-one | CH3 | H | 499 |
| 92 | 1,4-dimethyl-3-pyrrolin-2-one | CH3 | F | 517 |
| 93 | 2-acetylcyclopentanone | CH3 | H | 514 |
| 94 | 3,5,5-trimethylcyclopent-2-enone | CH3 | F | 530 |
| 95 | 4-methyl-2(5H)-furanone | CH3 | F | 504.1 |
| 96 | 5-hydroxy-3,5-dimethylcyclopent-2-enone | CH3 | F | 532.1 |
| 97 | 5-hydroxy-3,5-dimethylcyclopent-2-enone | CH3 | F | 532.1 |

-continued

[Structure: X-phenyl attached to pyrrolidine with R1 on N, and O-CH(R7)-(3,5-bis(trifluoromethyl)phenyl) substituent]

| Ex. # | R1 | R7 | X | parent ion (MH+) m/z |
|---|---|---|---|---|
| 98 | 4-hydroxy-2,3-dimethylcyclopent-2-enone | CH3 | F | 532.1 |
| 99 | 4-hydroxy-3-methyl-5-methylcyclopent-2-enone | CH3 | F | 532.1 |
| 100 | 4,5-dihydroxy-3,5-dimethylcyclopent-2-enone | CH3 | F | 548.0 |
| 101 | 4,5-dihydroxy-3,5-dimethylcyclopent-2-enone (isomer) | CH3 | F | 548.1 |
| 102 | 4,5-dihydroxy-3-methylcyclopent-2-enone | CH3 | F | 534.1 |
| 103 | 4,5-dihydroxy-3-methylcyclopent-2-enone (isomer) | CH3 | F | 534.1 |
| 104 | 2-methylpyrazine | CH3 | F | 500.0 |
| 105 | 2-pyridyl | CH3 | F | 499.1 |
| 106 | 3-pyridyl | CH3 | F | 499.0 |
| 107 | 3-methyl-2-oxocyclopent-3-enyl-CH2CO2Me | CH3 | F | 574.1 |
| 108 | 3-methyl-2-oxocyclopent-3-enyl-CH2CO2Me (isomer) | CH3 | F | 574.1 |
| 109 | 3-methyl-2-oxocyclopent-3-enyl-CH2CO2H | CH3 | F | 559.1 |
| 110 | methyl propanoate (CH2CH2C(O)OCH3) | CH3 | F | 494.2 |
| 111 | 2-methoxy-4-methylpyridyl | CH3 | F | 529.2 |
| 112 | 2-chloro-4-methylpyrimidin-?-yl | CH3 | F | 534.1 |
| 113 | 4-chloro-2-methylpyrimidin-?-yl | CH3 | F | 534.2 |
| 114 | 4-acetyl-3-oxopiperazinyl | CH3 | F | 548.0 |
| 115 | 3-acetyl-5-propylisoxazolyl | CH3 | F | 558.0 |
| 116 | 5-acetyl-1-methyl-3-ethylpyrazolyl | CH3 | F | 559.0 |

-continued

| Ex. # | R¹ | R⁷ | X | parent ion (MH⁺) m/z |
|---|---|---|---|---|
| 117 | 3-acetyl-2H-cyclopenta[c]pyrazole (HN-N fused cyclopentane with acetyl) | CH₃ | F | 556.0 |
| 118 | 6-acetyl-2-methyl-4,5-dihydropyridazin-3(2H)-one | CH₃ | F | 560.0 |
| 119 | 1-(3,5-dimethyl-1H-1,2,4-triazol-1-yl)propan-2-one | CH₃ | F | 559.6 |
| 120 | 1-(3,5-dimethyl-1H-pyrazol-1-yl)propan-2-one | CH₃ | F | 558.8 |
| 121 | 1-(1-methyl-1H-pyrazol-4-yl)ethanone | CH₃ | F | 530.0 |
| 122 | 1-(1-methyl-1H-pyrazol-5-yl)ethanone | CH₃ | F | 530.6 |
| 123 | 4-(3-methyl-1H-pyrazol-1-yl)butan-2-one | CH₃ | F | 558.0 |
| 124 | 7-acetylpyrazolo[1,5-a]pyridine | CH₃ | F | 566.6 |

-continued

| Ex. # | R¹ | R⁷ | X | parent ion (MH⁺) m/z |
|---|---|---|---|---|
| 125 | 3-(1H-1,2,4-triazol-1-yl)butan-2-one | CH₃ | F | 545.0 |
| 126 | 3-acetylcyclobutan-1-one | CH₃ | F | 518.5 |
| 127 | 1-(3-methyl-1H-pyrazol-1-yl)propan-2-one | CH₃ | F | 544.0 |
| 128 | 1-(1,3-dimethyl-1H-pyrazol-5-yl)ethanone | CH₃ | F | 544.2 |
| 129 | 1-(5-methyl-1H-pyrazol-1-yl)propan-2-one | CH₃ | F | 544.0 |
| 130 | 1-(5-methyl-1H-1,2,4-triazol-3-yl)propan-2-one | CH₃ | F | 545.0 |
| 131 | 1-(pyrazin-2-yl)ethanone | CH₃ | F | 528.0 |
| 132 | 1-(furan-2-yl)ethanone | CH₃ | F | 516.0 |
| 133 | 1-(thiophen-2-yl)ethanone | CH₃ | F | 532.0 |

-continued

[Structure: X-phenyl-pyrrolidine with R¹ on N, and O-CH(R⁷)-3,5-bis(trifluoromethyl)phenyl substituent]

| Ex. # | R¹ | R⁷ | X | parent ion (MH⁺) m/z |
|---|---|---|---|---|
| 134 | acetyl-1,2,5-thiadiazol-3-yl | CH₃ | F | 534.0 |
| 135 | acetyl-thiophen-3-yl | CH₃ | F | 532.0 |
| 136 | acetyl-pyrimidin-5-yl | CH₃ | F | 527.9 |
| 137 | acetyl-pyrimidin-4-yl | CH₃ | F | 528.1 |
| 138 | acetyl-1H-benzimidazol-2-yl | CH₃ | F | 566.0 |
| 139 | acetyl-1H-1,2,3-triazol-4-yl | CH₃ | F | 517.2 |
| 140 | acetyl-pyrazolo[1,5-a]pyrimidin-3-yl | CH₃ | F | 567.0 |
| 141 | 1-methyl-3-propyl-1H-pyrazol-5-yl acetyl | CH₃ | F | 572.0 |
| 142 | acetyl-5,6,7,8-tetrahydro-1,8-naphthyridin-2-yl | CH₃ | F | 582.2 |
| 143 | acetyl-2-(methylthio)thiazol-4-yl | CH₃ | F | 579.1 |
| 144 | (4-methylthiazol-2-ylthio)acetone | CH₃ | F | 592.9 |
| 145 | acetyl-4-oxo-3,4-dihydrophthalazin-1-yl | CH₃ | F | 593.9 |
| 146 | acetyl-4,5,6,7-tetrahydrobenzo[d]isoxazol-3-yl | CH₃ | F | 571.2 |
| 147 | acetyl-2,3-dihydrobenzo[b][1,4]dioxin-6-yl | CH₃ | F | 584.2 |
| 148 | acetyl-2-(1H-tetrazol-1-yl)pyridin-4-yl | CH₃ | F | 595.0 |
| 149 | 5-(1H-1,2,4-triazol-1-yl)pentan-2-one | CH₃ | F | 559.2 |

-continued

| Ex. # | R¹ | R⁷ | X | parent ion (MH⁺) m/z |
|---|---|---|---|---|
| 150 | 4-(2-oxopropyl)-2H-pyridazine-3,6-dione | CH₃ | F | 574.2 |
| 151 | 1-(2-oxopropyl)-1H-pyridazine-3,6-dione | CH₃ | F | 573.9 |
| 152 | 1-(2,4-dimethylthiazol-5-yl)propan-2-one | CH₃ | F | 575.0 |
| 153 | 3-acetyl-4H-pyrido[1,2-a]pyrimidin-4-one | CH₃ | F | 594.1 |
| 154 | 1-(2-(1H-tetrazol-1-yl)phenyl)ethanone | CH₃ | F | 594.1 |
| 155 | 1-(4-(1H-tetrazol-1-yl)phenyl)ethanone | CH₃ | F | 594.0 |
| 156 | 1-(2,3-dihydrobenzo[b][1,4]dioxin-2-yl)ethanone | CH₃ | F | 584.0 |
| 157 | 3-(2-oxopropyl)benzo[d]oxazol-2(3H)-one | CH₃ | F | 597.1 |
| 158 | 1-(3-(1H-tetrazol-1-yl)phenyl)ethanone | CH₃ | F | 594.1 |
| 159 | 6-acetyl-5H-thiazolo[3,2-a]pyrimidin-5-one | CH₃ | F | 600.0 |
| 160 | 1-(benzo[d]thiazol-2-yl)ethanone | CH₃ | F | 582.9 |
| 161 | 1-(3-oxo-2,3-dihydro-1H-isoindol-1-yl)propan-2-one | CH₃ | F | 595.2 |
| 162 | 4-(3,5-dimethyl-1H-pyrazol-1-yl)butan-2-one | CH₃ | F | 572.2 |
| 163 | 1-(2-oxo-1,2-dihydroquinazolin-4-yl)ethanone | CH₃ | F | 594.1 |

-continued
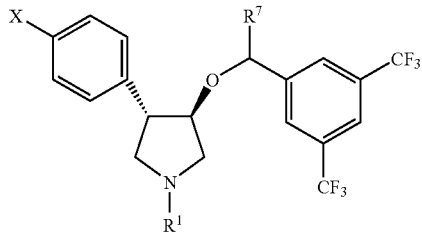
| Ex. # | R¹ | R⁷ | X | parent ion (MH⁺) m/z |
|---|---|---|---|---|
| 164 | 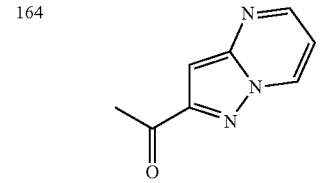 | CH₃ | F | 567.1 |
| 165 | 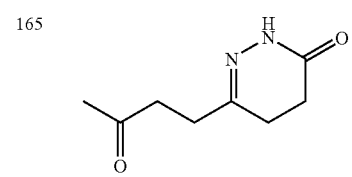 | CH₃ | F | 574.0 |
| 166 | 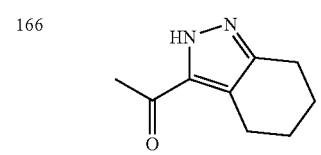 | CH₃ | F | 570.2 |
| 167 | 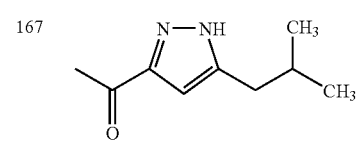 | CH₃ | F | 572.2 |
| 168 | 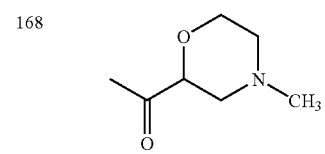 | CH₃ | F | 549.0 |
| 169 | 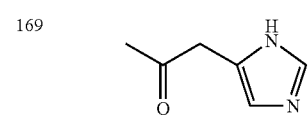 | CH₃ | F | 529.0 |
| 170 | 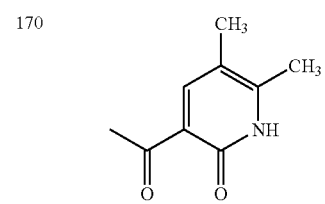 | CH₃ | F | 571.2 |
| 171 | 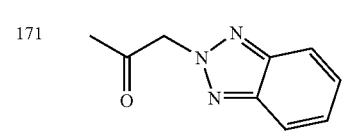 | CH₃ | F | 581.0 |
-continued
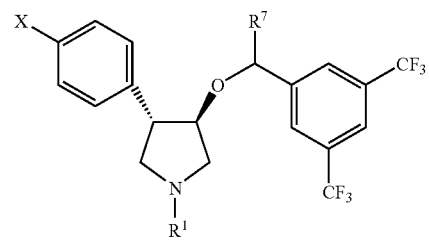
| Ex. # | R¹ | R⁷ | X | parent ion (MH⁺) m/z |
|---|---|---|---|---|
| 172 | 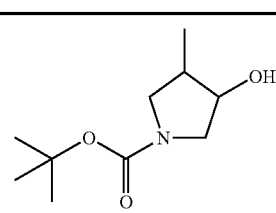 | CH₃ | F | 607.2 |
| 173 | 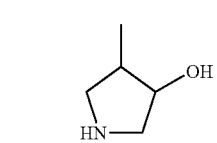 | CH₃ | F | 507.1 |
| 174 | 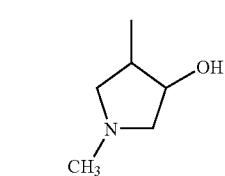 | CH₃ | F | 521.5 |
| 175 | 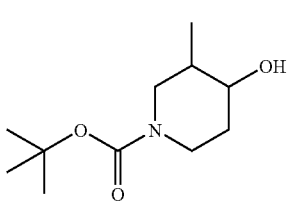 | CH₃ | F | 621.2 |
| 176 | 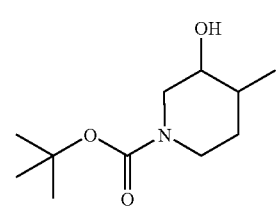 | CH₃ | F | 621.2 |
| 177 | 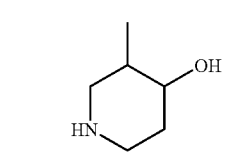 | CH₃ | F | 521.0 |
| 178 | 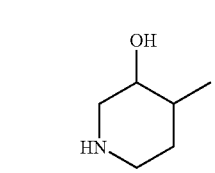 | CH₃ | F | 521.0 |

-continued
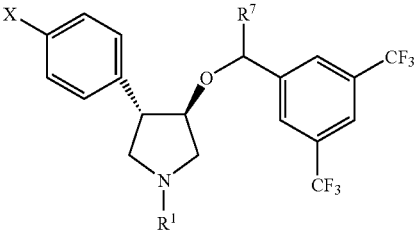
| Ex. # | R¹ | R⁷ | X | parent ion (MH⁺) m/z |
|---|---|---|---|---|
| 179 | 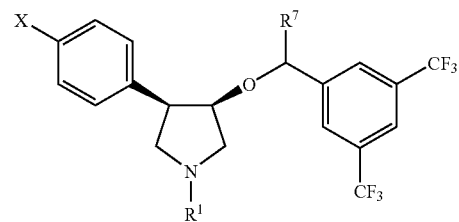 | CH₃ | F | 535.2 |
| 180 | 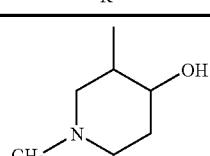 | CH₃ | F | 535.2 |
Using the procedures comparable to those described above the following Examples were prepared.
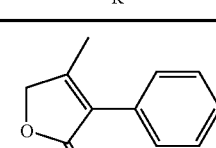
| Ex. # | R¹ | R⁷ | X | parent ion (MH⁺) m/z |
|---|---|---|---|---|
| 181 | 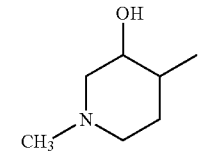 | CH₃ | F | 464 |
| 182 | 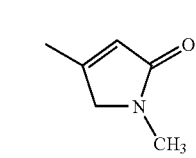 | CH₃ | F | 516 |
| 183 | H | CH₃ | F | 422 |
| 184 | 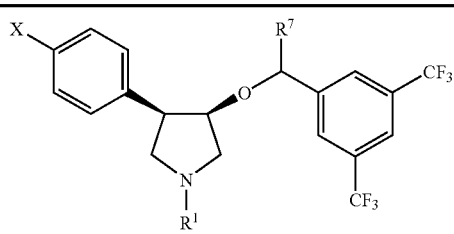 | CH₃ | F | 493 |
| 185 | 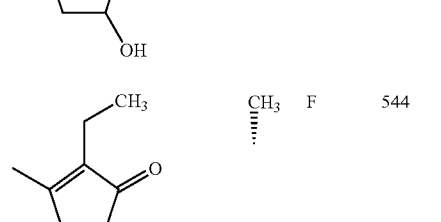 | CH₃ | F | 504 |
-continued
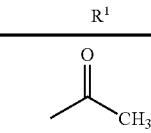
| Ex. # | R¹ | R⁷ | X | parent ion (MH⁺) m/z |
|---|---|---|---|---|
| 186 | 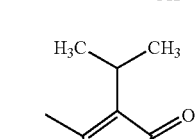 | CH₃ | F | 580 |
| 187 | 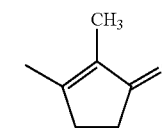 | CH₃ | F | 517 |
| 188 | 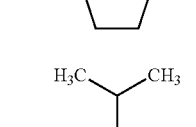 | CH₃ | F | 546 |
| 189 | 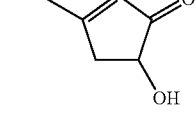 | CH₃ | F | 544 |
| 190 | 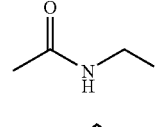 | CH₃ | F | 544 |
| 191 | 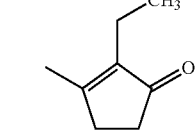 | CH₃ | F | 560 |
| 192 | 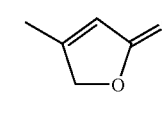 | CH₃ | F | 530 |

-continued
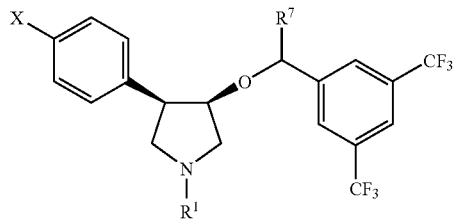
| Ex. # | R¹ | R⁷ | X | parent ion (MH⁺) m/z |
|---|---|---|---|---|
| 193 | 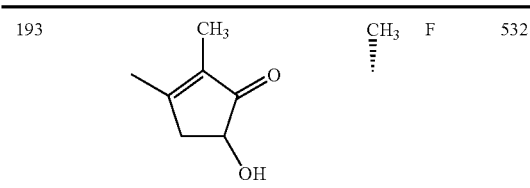 | CH₃ | F | 532 |
| 194 | 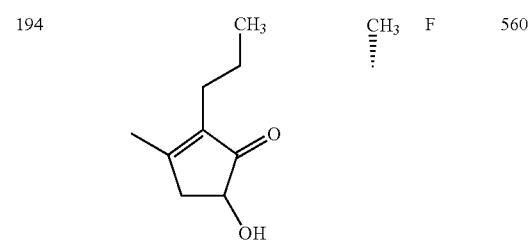 | CH₃ | F | 560 |
| 195 | 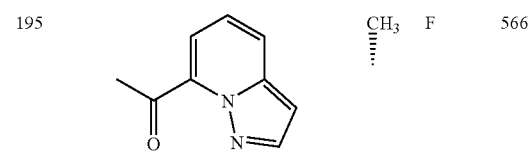 | CH₃ | F | 566 |
| 196 | 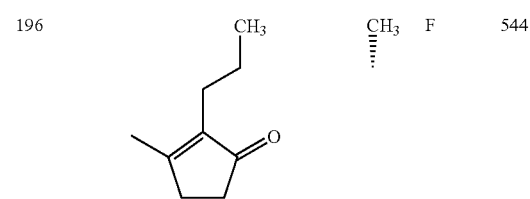 | CH₃ | F | 544 |
| 197 | 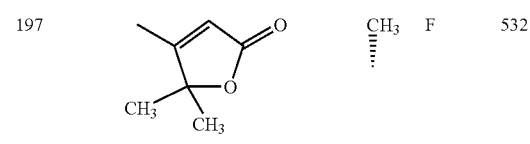 | CH₃ | F | 532 |
| 198 | 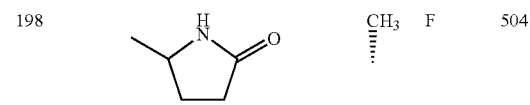 | CH₃ | F | 504 |
| 199 | 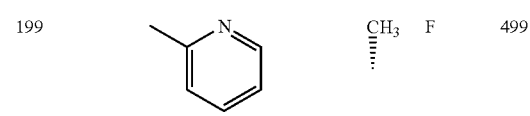 | CH₃ | F | 499 |
| 200 | 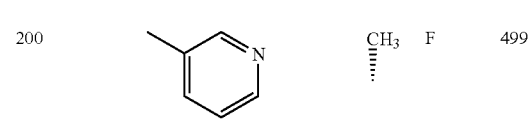 | CH₃ | F | 499 |
-continued
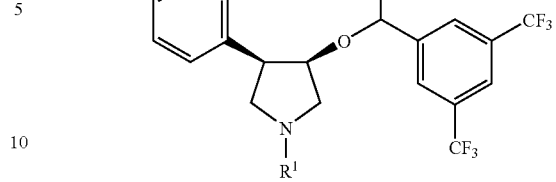
| Ex. # | R¹ | R⁷ | X | parent ion (MH⁺) m/z |
|---|---|---|---|---|
| 201 | 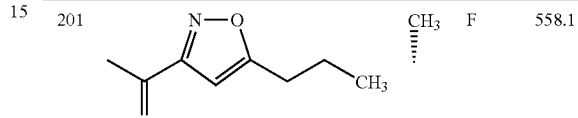 | CH₃ | F | 558.1 |
| 202 | 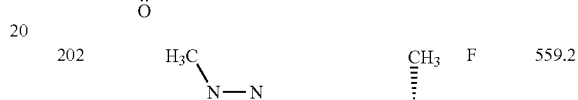 | CH₃ | F | 559.2 |
| 203 | 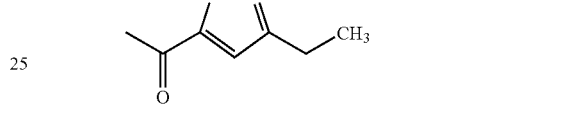 | CH₃ | F | 556.0 |
| 204 | 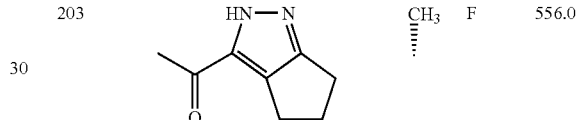 | CH₃ | F | 560.0 |
| 205 | 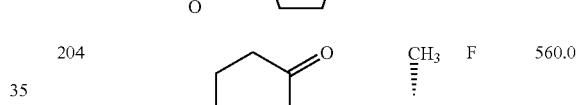 | CH₃ | F | 558.0 |
| 206 | 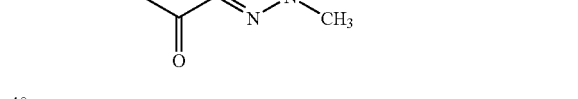 | CH₃ | F | 530.0 |
| 207 | 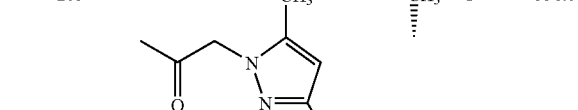 | CH₃ | F | 567.0 |
| 208 | 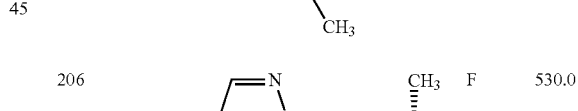 | CH₃ | F | 530.0 |

-continued

| Ex. # | R¹ | R⁷ | X | parent ion (MH⁺) m/z |
|---|---|---|---|---|
| 209 | 2-acetyl-benzimidazole | CH₃ | F | 566.0 |
| 210 | 1-(3-methylpyrazol-1-yl)butan-2-one | CH₃ | F | 558.1 |
| 211 | 4-acetylpyrimidine | CH₃ | F | 528.1 |
| 212 | 7-acetylpyrazolo[1,5-a]pyridine | CH₃ | F | 566.1 |
| 213 | 5-acetylpyrimidine | CH₃ | F | 528.0 |
| 214 | 1-(1,2,4-triazol-1-yl)propan-2-one | CH₃ | F | 545.0 |
| 215 | 2-acetylthiophene | CH₃ | F | 532.0 |
| 216 | 3-acetylcyclobutanone | CH₃ | F | 518.0 |
| 217 | 2-acetylfuran | CH₃ | F | 516.0 |

| Ex. # | R¹ | R⁷ | X | parent ion (MH⁺) m/z |
|---|---|---|---|---|
| 218 | 1-(3-methylpyrazol-1-yl)propan-2-one | CH₃ | F | 544.0 |
| 219 | 2-acetylpyrazine | CH₃ | F | 528.0 |
| 220 | 1-(1,3-dimethylpyrazol-5-yl)ethanone | CH₃ | F | 544.2 |
| 221 | 1-(5-methyl-1,2,4-triazol-3-yl)propan-2-one | CH₃ | F | 545.0 |
| 222 | 1-(5-methylpyrazol-1-yl)propan-2-one | CH₃ | F | 544.0 |

Using the procedures comparable to those described above the following Examples as shown in the Table were prepared in racemic form (mixture) or as a single enantiomer by separation by chiral chromatography.

| Ex. # | Structure | parent ion (MH⁺) m/z |
|---|---|---|
| 223 | 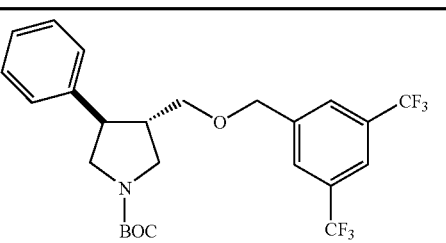 | 448.9 |

| Ex. # | Structure | parent ion (MH+) m/z |
|---|---|---|
| 224 | 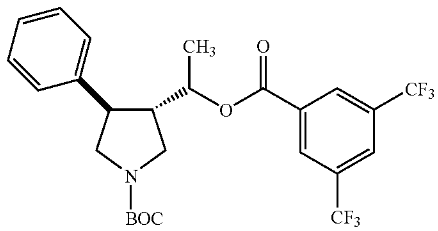 | not observed |
| 225 | 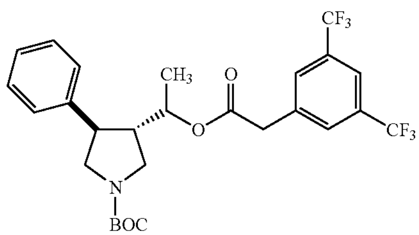 | 568.1 (M + Na+) 490.1 (M-tBu) |
| 226 | 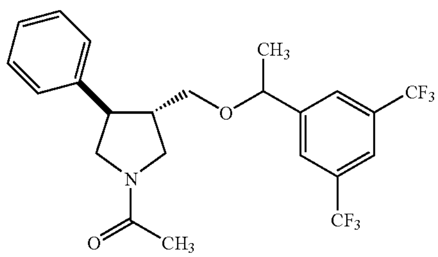 | 460.1 |
| 227 | 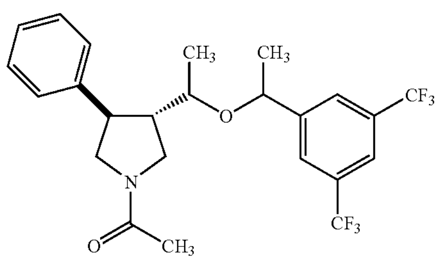 | 474.1 |
| 228 | 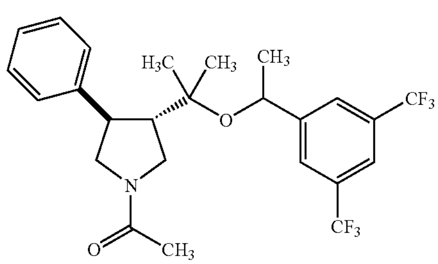 | 488.1 |
| 229 | 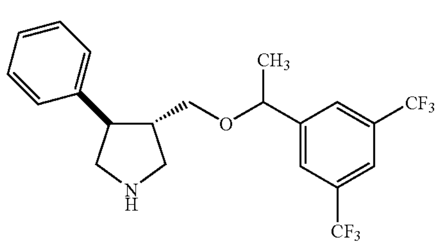 | 417.8 |
| 230 | | 460.0 |
| 231 | | 460.0 |
| 232 | | 602.9 |
| 233 | | 450.1 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

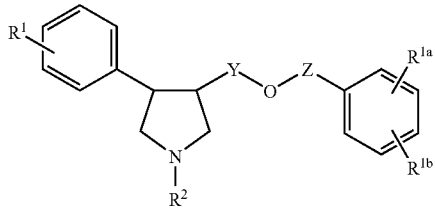

wherein:
$R^1$, $R^{1a}$ and $R^{1b}$ are independently selected from the group consisting of H, F, Cl, Br, I, $CH_3$, $CF_3$, OH, $OCH_3$, $NH_2$, $NHCH_3$, SH, and $SCH_3$;
$R^2$ is selected from the group consisting of H, $R^4$, $COR^4$, and $SO_2R^4$;
Y is a bond, $CHCH_3$, or $CH_2$;
Z is selected from the group consisting of $CH_2$, $CHCH_3$, CO, and $COCH_2$;
$R^4$ is independently selected from the group consisting of H, $C_{1-6}$alkyl, phenyl optionally substituted by $R^6$, benzyl, O—$C_{1-6}$alkyl, O-benzyl, $N(R^5)$—$C_{1-6}$alkyl, $N(R^5)$-benzyl,

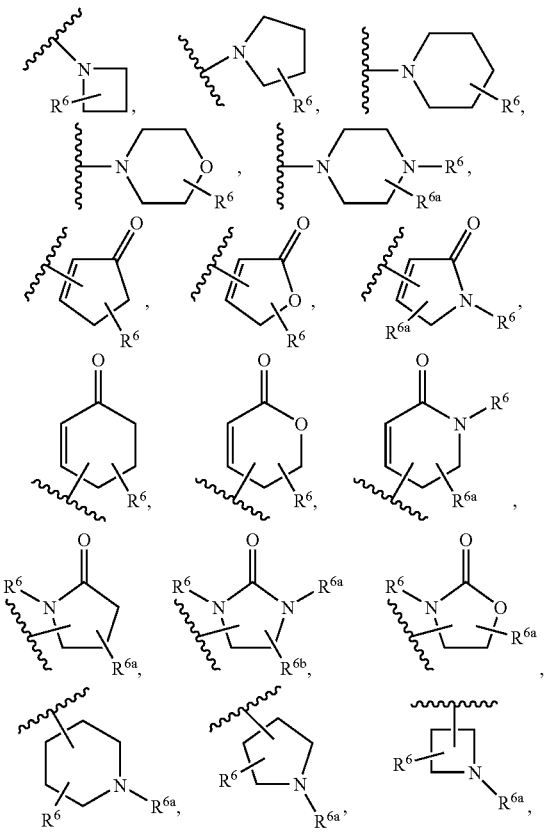

-continued

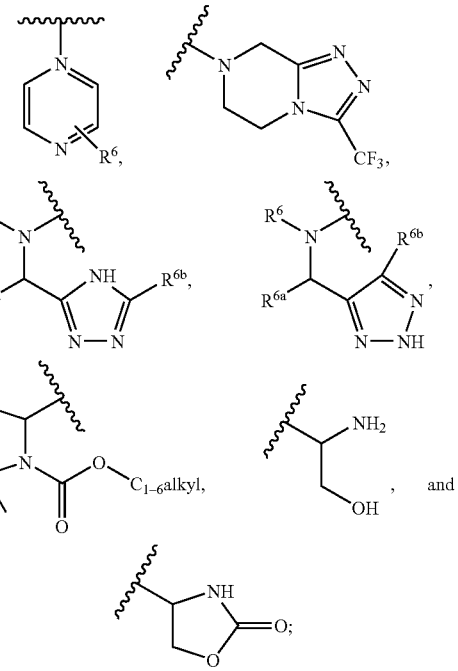

$R^5$ is H or $C_{1-6}$alkyl;
$R^6$, $R^{6a}$, and $R^{6b}$ are independently selected from the group consisting of H, F, Cl, $CF_3$, $OCH_3$, $CH_3$, $COCH_3$, $CO_2CH_3$, $CH_2CONH_2$, $CONH_2$, $CONHCH_3$, and $SO_2CH_3$;
and pharmaceutically acceptable salts thereof.

2. The compound of claim 1 of the formula Ia:

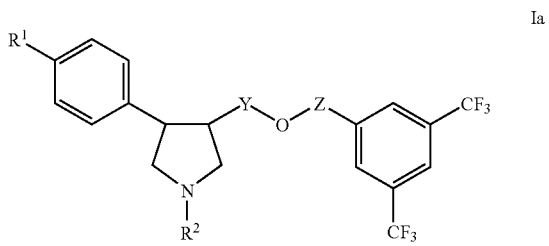

wherein Y, Z, $R^1$, $R^2$, and $R^3$ are as defined in claim 1.

3. The compound of claim 2 wherein Y is a bond.

4. The compound of claim 3 wherein $R^1$ is H or F.

5. The compound of claim 4 wherein $R^2$ is $R^4$.

6. The compound of claim 5 wherein $R^4$ is selected from the group consisting of:

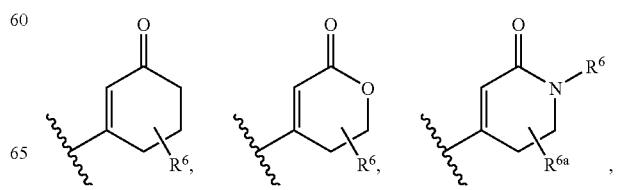

-continued

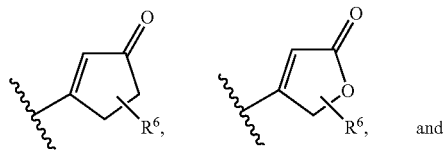

and

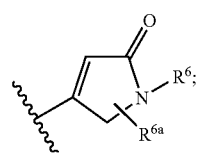

wherein R⁶ and R⁶ᵃ are independently selected from the group consisting of H, F, Cl, CF$_3$, OCH$_3$, CH$_3$, COCH$_3$, CO$_2$CH$_3$, CH$_2$CONH$_2$, CONH$_2$, CONHCH$_3$, and SO$_2$CH$_3$.

7. The compound of claim 4 wherein $R^2$ is $COR^4$.

8. The compound of claim 7 wherein $R^4$ is selected from the group consisting of:

—NHCH$_3$, —NHCH$_2$CH$_3$, —N(CH$_3$)$_2$, —OCH$_3$, —OC(CH$_3$)$_3$, —CH$_3$, —CH$_2$CH$_3$, —CH(CH$_3$)$_2$,

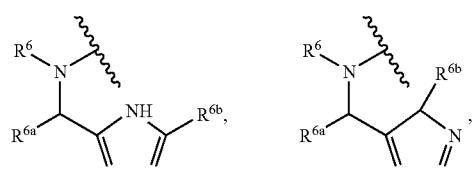

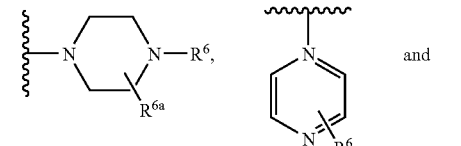

and

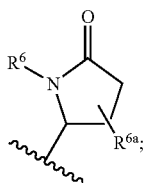

wherein $R^6$, $R^{6a}$, and $R^{6b}$ are independently selected from the group consisting of H, F, Cl, CF$_3$, OCH$_3$, CH$_3$, COCH$_3$, CO$_2$CH$_3$, CH$_2$CONH$_2$, CONH$_2$, CONHCH$_3$, and SO$_2$CH$_3$.

9. A compound which is selected from the group consisting of:

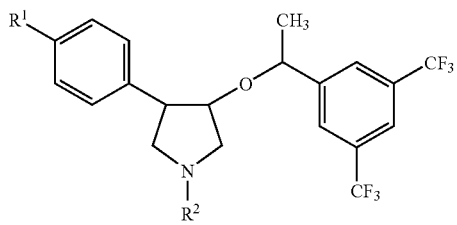

wherein $R^2$ and $R^1$ are selected from the table below:

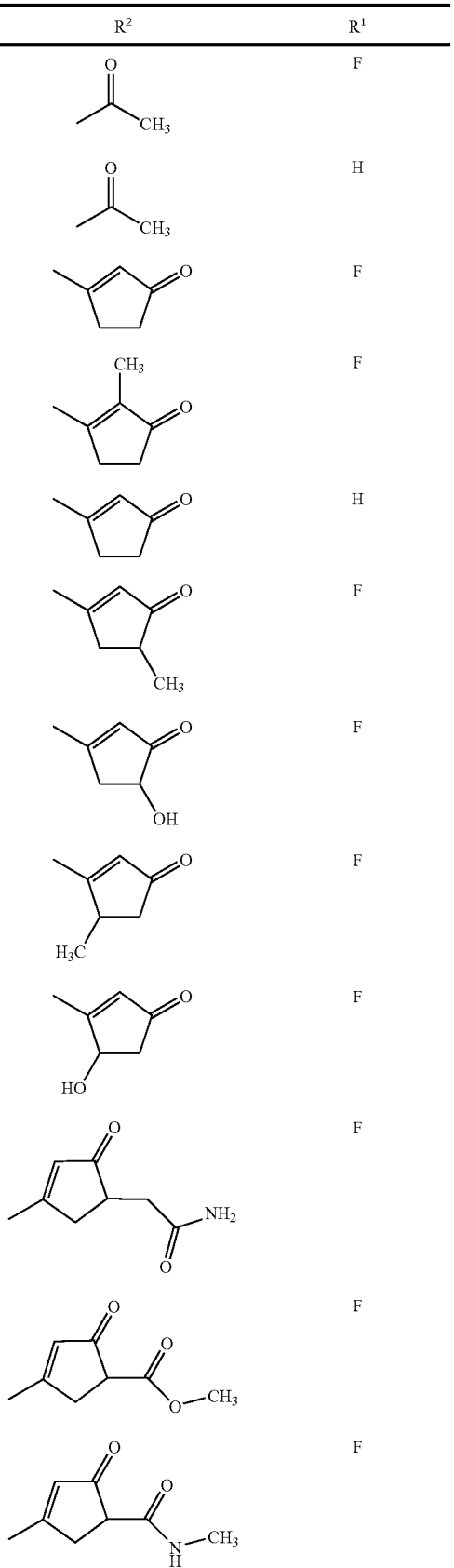

| $R^2$ | $R^1$ |
|---|---|
| acetyl | F |
| acetyl | H |
| 3-methyl-2-cyclopentenonyl | F |
| 2,3-dimethyl-2-cyclopentenonyl | F |
| 3-methyl-2-cyclopentenonyl | H |
| 3,5-dimethyl-2-cyclopentenonyl | F |
| 3-methyl-5-hydroxy-2-cyclopentenonyl | F |
| 3-methyl-4-methyl-2-cyclopentenonyl | F |
| 3-methyl-5-hydroxy-2-cyclopentenonyl | F |
| 3-methyl-2-cyclopentenonyl-acetamide | F |
| 3-methyl-2-cyclopentenonyl-methylester | F |
| 3-methyl-2-cyclopentenonyl-N-methylamide | F |

79

(chemical structures with F/H substituents)

80

(chemical structures, all with F substituent)

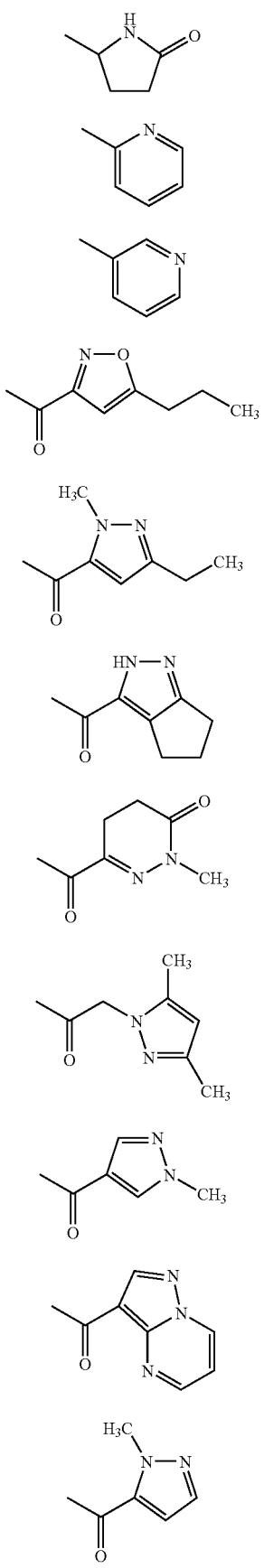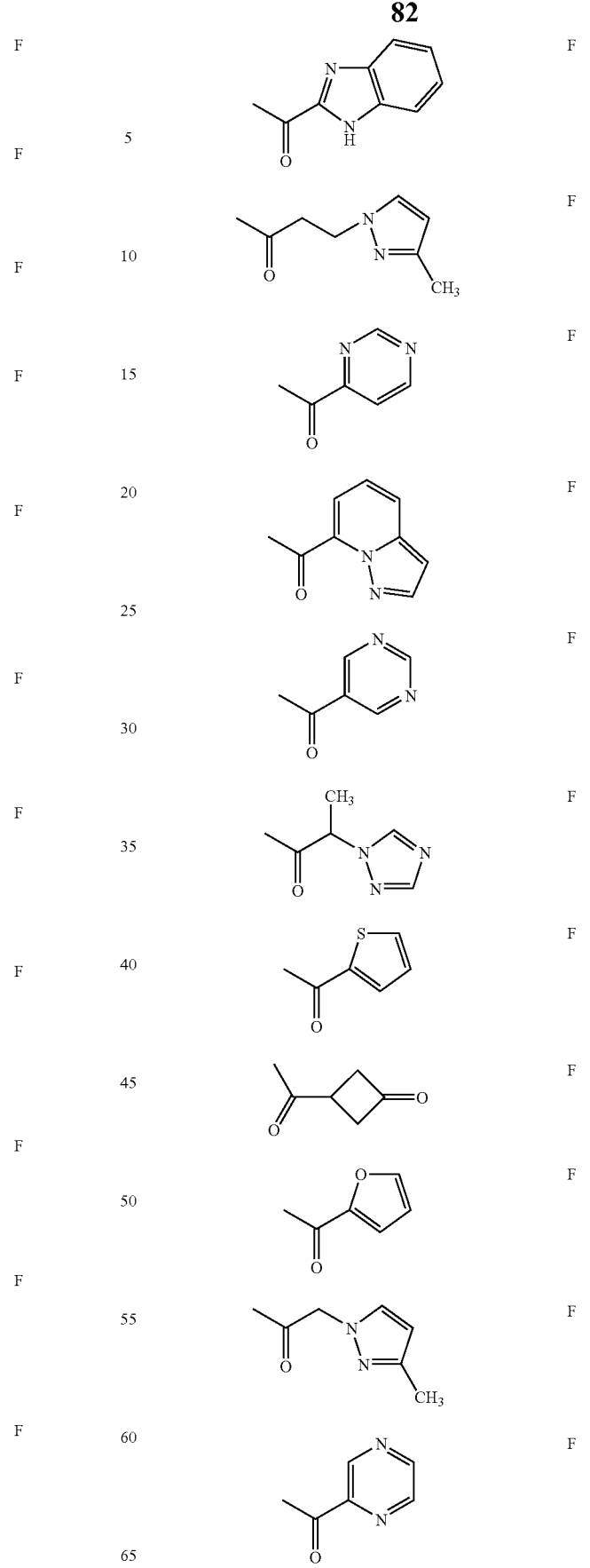

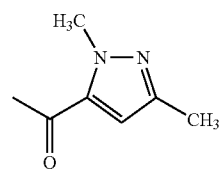

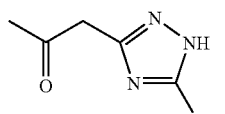

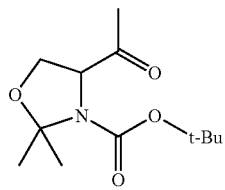

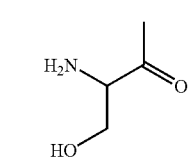

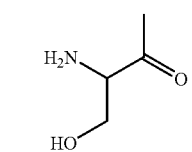

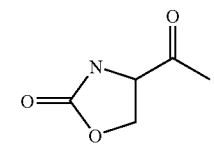

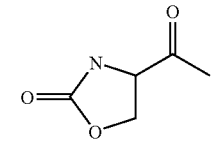

and

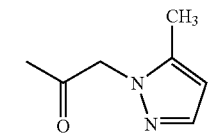

and pharmaceutically acceptable salts thereof.

10. A compound which is selected from the group consisting of:

(3R,4S)-1-Acetyl-3-({(1R)-1-[3,5-bis(trifluoromethyl) phenyl]ethyl}oxy)-4-phenylpyrrolidine;

(3R,4S)-3-({(1R)-1-[3,5-Bis(trifluoromethyl)phenyl] ethyl}oxy)-4-(4-fluorophenyl)-N-methylpyrrolidine-1-carboxamide;

3-[(3R,4S)-3-({(1R)-1-[3,5-Bis(trifluoromethyl)phenyl] ethyl}oxy)-4-(4-fluorophenyl)pyrrolidin-1-yl]cyclopent-2-en-1-one;

tert-Butyl 4-{[(3R,4S)-3-({(1R)-1-[3,5-bis(trifluoromethyl)phenyl]ethyl}oxy)-4-phenylpyrrolidin-1-yl]carbonyl}-2,2-dimethyl-1,3-oxazolidine-3-carboxylate;

2-Amino-3-[(3R,4S)-3-({(1R)-1-[3,5-bis(trifluoromethyl)phenyl]ethyl}oxy)-4-phenylpyrrolidin-1-yl]-3-oxopropan-1-ol;

4-{[(3R,4S)-3-({(1R)-1-[3,5-Bis(trifluoromethyl)phenyl] ethyl}oxy)-4-phenylpyrrolidin-1-yl]carbonyl}-1,3-oxazolidin-2-one;

3-[(3R,4R)-3-({(1R)-1-[3,5-Bis(trifluoromethyl)phenyl] ethyl}oxy)-4-(4-fluorophenyl)pyrrolidin-1-yl]cyclopent-2-en-1-one;

(5R)-3-[(3R,4S)-3-({(1R)-1-[3,5-Bis(trifluoromethyl) phenyl]ethyl}oxy)-4-(4-fluorophenyl)pyrrolidin-1-yl]-5-methylcyclopent-2-en-1-one;

(5S)-3-[(3R,4S)-3-({(1R)-1-[3,5-Bis(trifluoromethyl) phenyl]ethyl}oxy)-4-(4-fluorophenyl)pyrrolidin-1-yl]-5-methylcyclopent-2-en-1-one;

(5R)-3-[(3R,4S)-3-({(1R)-1-[3,5-Bis(trifluoromethyl) phenyl]ethyl}oxy)-4-(4-fluorophenyl)pyrrolidin-1-yl]-5-hydroxycyclopent-2-en-1-one;

(5S)-3-[(3R,4S)-3-({(1R)-1-[3,5-Bis(trifluoromethyl) phenyl]ethyl}oxy)-4-(4-fluorophenyl)pyrrolidin-1-yl]-5-hydroxycyclopent-2-en-1-one;

3-[(3R,4S)-3-({(1R)-1-[3,5-Bis(trifluoromethyl)phenyl] ethyl}oxy)-4-(4-fluorophenyl)pyrrolidin-1-yl]-4-methylcyclopent-2-en-1-one;

(4R)-3-[(3R,4S)-3-({(1R)-1-[3,5-Bis(trifluoromethyl) phenyl]ethyl}oxy)-4-(4-fluorophenyl)pyrrolidin-1-yl] hydroxycyclopent-2-en-1-one;

2-{2-[(3R,4S)-3-({(1R)-1-[3,5-Bis(trifluoromethyl)phenyl]ethyl}oxy)-4-(4-fluorophenyl)pyrrolidin-1-yl]-5-oxocyclopent-1-en-1-yl}acetamide;

Methyl 2-[(3R,4S)-3-({(1R)-1-[3,5-bis(trifluoromethyl) phenyl]ethyl}oxy)-4-(4-fluorophenyl)pyrrolidin-1-yl]-5-oxocyclopent-1-ene-1-carboxylate; and 2-[(3R,4S)-3-({(1R)-1-[3,5-Bis(trifluoromethyl)phenyl] ethyl}oxy)-4-(4-fluorophenyl)pyrrolidin-1-yl]-N-methyl-5-oxocyclopent-1-ene-1-carboxamide.

11. A pharmaceutical composition comprising a pharmaceutically acceptable carrier and a therapeutically effective amount of a compound of claim 1.

12. A method for antagonizing the effect of substance P at its receptor site or for the blockade of neurokinin-1 receptors in a mammal which comprises the administration to the mammal of the compound of claim 1 in an amount that is effective for antagonizing the effect of substance P at its receptor site in the mammal.

13. A method for the treatment of emesis in a mammal in need thereof which comprises the administration to the mammal of a therapeutically effective amount of the compound of claim 1.

* * * * *